(12) United States Patent
Niedernhofer et al.

(10) Patent No.: US 9,220,711 B2
(45) Date of Patent: *Dec. 29, 2015

(54) COMPOUNDS FOR THE TREATMENT OF PATHOLOGIES ASSOCIATED WITH AGING AND DEGENERATIVE DISORDERS

(71) Applicant: University of Pittsburgh—Of the Commonwealth System of Higher Education, Pittsburgh, PA (US)

(72) Inventors: Laura J. Niedernhofer, Pittsburgh, PA (US); Paul D. Robbins, Pittsburgh, PA (US); Peter Wipf, Pittsburgh, PA (US)

(73) Assignee: University of Pittsburgh—of the Commonwealth System of Higher Education, Pittsburgh, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/218,784

(22) Filed: Mar. 18, 2014

(65) Prior Publication Data

US 2015/0018346 A1 Jan. 15, 2015

Related U.S. Application Data

(60) Division of application No. 12/930,702, filed on Jan. 14, 2011, now Pat. No. 8,937,086, which is a continuation of application No. PCT/US2009/050869, filed on Jul. 16, 2009.

(60) Provisional application No. 61/081,678, filed on Jul. 17, 2008.

(51) Int. Cl.
| | |
|---|---|
| *A01N 43/40* | (2006.01) |
| *A61K 31/445* | (2006.01) |
| *A61K 8/49* | (2006.01) |
| *A61Q 19/08* | (2006.01) |
| *A61K 31/40* | (2006.01) |
| *A61K 31/454* | (2006.01) |
| *A61K 31/54* | (2006.01) |
| *A61K 31/541* | (2006.01) |

(52) U.S. Cl.
CPC ............. *A61K 31/445* (2013.01); *A61K 8/4926* (2013.01); *A61K 31/40* (2013.01); *A61K 31/454* (2013.01); *A61K 31/54* (2013.01); *A61K 31/541* (2013.01); *A61Q 19/08* (2013.01)

(58) Field of Classification Search
None
See application file for complete search history.

(56) References Cited

U.S. PATENT DOCUMENTS

| | | | |
|---|---|---|---|
| 4,548,973 A | 10/1985 | Raynor | |
| 5,134,165 A | 7/1992 | Hirsch-Kauffmann | |
| 5,552,415 A | 9/1996 | May | |
| 6,117,634 A | 9/2000 | Langmore et al. | |
| 6,610,723 B2 | 8/2003 | Alamine et al. | |
| 6,762,158 B2 | 7/2004 | Lukenbach et al. | |
| 6,939,880 B2 | 9/2005 | Hansen et al. | |
| 7,176,239 B2 | 2/2007 | Wang et al. | |
| 7,528,174 B2 | 5/2009 | Wipf et al. | |
| 7,718,603 B1 | 5/2010 | Wipf et al. | |
| 8,288,551 B2 | 10/2012 | Wipf et al. | |
| 8,487,079 B2 * | 7/2013 | Fink et al. ...................... 530/330 |
| 2002/0052399 A1 | 5/2002 | Vazquez et al. | |
| 2005/0020633 A1 | 1/2005 | Maxwell et al. | |
| 2007/0161544 A1* | 7/2007 | Wipf et al. ......................... 514/8 |
| 2007/0161573 A1* | 7/2007 | Wipf et al. ....................... 514/17 |
| 2008/0045470 A1 | 2/2008 | Bielawska et al. | |
| 2011/0039792 A1 | 2/2011 | Wipf et al. | |
| 2011/0172214 A1 | 7/2011 | Wipf et al. | |
| 2012/0004263 A1 | 1/2012 | Niedernhofer et al. | |

FOREIGN PATENT DOCUMENTS

WO WO 2010/009389 1/2010

OTHER PUBLICATIONS

Lin et al., "Mitochondrial dysfunction and oxidative stress in neurodegenerative diseases," vol. 443, Oct. 19, 2006.*
Kirkinezos et al., "Reactive oxygen species and mitochondrial diseases," Cell and Development Biology, vol. 12, 2001: pp. 449-457.*
Saha et al.,"Regulation of Inducible Nitric Oxide Synthase Gene in Glial Cells," Antioxid Redox Signal. 2006; 8(5-6): 929-947.*
European Supplemental Search Report from corresponding European Application No. 09798808.3 dated Feb. 22, 2012.
Fink et al., "Hemigramicidin-TEMPO conjugates: Novel mitochondria-targeted anti-oxidants," *Biochemical Pharmacology* 74(6):81-809, Sep. 15, 2007.
Hahn et al., "Potential Use of Nitroxides in Radiation Oncology," *Cancer Research* 54:2006s-2010s, Apr. 1, 1994.
Hahn et al., "Tempol, a Stable Free Radical, Is a Novel Murine Radiation Protector," *Cancer Research* 52:1750-1753, 1992.
International Preliminary Report on Patentability from PCT Application No. PCT/US2009/051004, dated Jan. 18, 2011.

(Continued)

*Primary Examiner* — Craig Ricci
*Assistant Examiner* — Jared D Barsky
(74) *Attorney, Agent, or Firm* — Klarquist Sparkman, LLP

(57) ABSTRACT

The present invention relates to methods of inhibiting one or more signs of aging and/or degenerative disorder in a subject in need of such treatment, which comprise administering, to the subject, an effective amount of one or more of the compounds as set forth herein. "Inhibiting a sign of aging or degenerative disorder" means reducing the risk of occurrence, delaying the onset, slowing the progression, and/or reducing the severity and/or manifestation, of a sign of aging or degenerative disorder, and includes, but is not limited to, preventing the occurrence, development or progression of a sign of aging or degenerative disorder.

5 Claims, 39 Drawing Sheets

(56) References Cited

OTHER PUBLICATIONS

International Preliminary Report on Patentability from PCT Application No. PCT/US2009/050983, dated Jan. 18, 2011.
International Search Report from PCT Application No. PCT/US2009/051004, mailed Mar. 12, 2010.
Jiang et al., "Structural Requirements for Optimized Delivery, Inhibition of Oxidative Stress, and Antiapoptotic Activity of Targeted Nitroxides," *The Journal of Pharmacology and Experimental Therapeutics* 320(3):1050-1060, Mar. 1, 2007.
Krishna et al., "Do Nitroxide Antioxidants Act as Scavengers of $O_2$ or as SOD Mimics?" *The Journal of Biological Chemistry* 271(42):26026-26031, 1996.
Macias et al., "Treatment with a Novel Hemigramicidin-TEMPO Conjugate Prolongs Survival in a Rat Model of Lethal Hemorrhagic Shock," *Annals of Surgery* 245(2):305-314, Feb. 1, 2007.
Mitchell et al., "Radiation, Radicals, and Images," *Annals New York Academy of Sciences* 899:28-43, 2000.
Non-Final Office Action dated Jan. 25, 2013, from U.S. Appl. No. 13/006,640.
Rodier et al., "Four Faces of cellular senescence," *Journal of Cell Biology*, Feb. 14, 2011.
Wipf et al., "Convergent Approach to ($E$)-Alkene and Cyclopropane Peptide Isosteres," *Organic Letters* 7(1):103-106, 2005.
Wipf et al., "Mitochondria Targeting of Selective Electron Scavengers: Synthesis and Biological Analysis of Hemigramicidin—TEMPO Conjugates," *JACS* 127(36):12460-12461, Sep. 1, 2005 (Published online Aug. 15, 2005).
Written Opinion of the International Search Authority from PCT Application No. PCT/US2009/051004, mailed Mar. 12, 2010.

\* cited by examiner

XJB-5-131

JP4-039

JED-E71-58

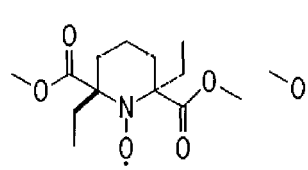 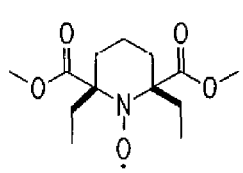 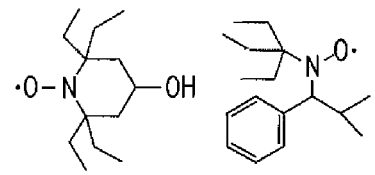
G1, LogP=2.0  G2, LogP=2.5  G3, LogP=3.4  G4, LogP=5.4
FIG. 2A-1a  FIG. 2A-1b  FIG. 2A-1c  FIG. 2A-1d
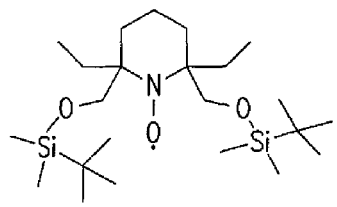 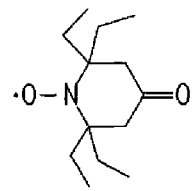 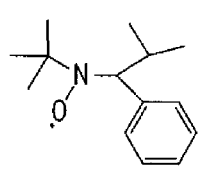
G5, LogP=8.2  G6, LogP=3.2  TIPNO-1, LogP=3.9
FIG. 2A-1e  FIG. 2A-1f  FIG. 2A-1g
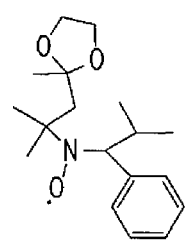 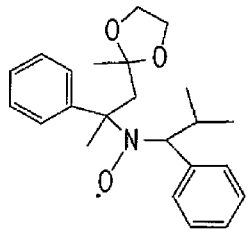 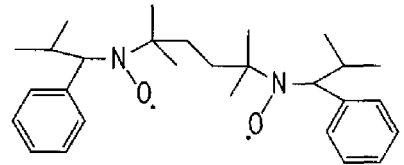
TIPNO-2, LogP=3.6  TIPNO-3, LogP=4.8  Bis-TIPNO, LogP=7.3
FIG. 2A-1h  FIG. 2A-1i  FIG. 2A-1j

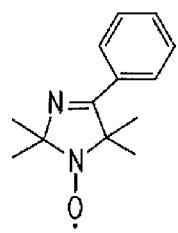 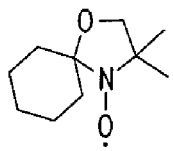 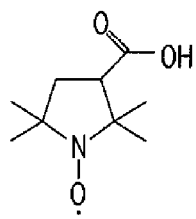 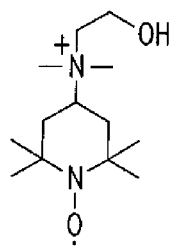
Nitronyl nitroxide, LogP=1.7
Doxyl radical, LogP=2.6
3-carboxyl-PROXYL, LogP=1.4
TEMPO choline, LogP=2.5
FIG. 2A-2a   FIG. 2A-2b   FIG. 2A-2c   FIG. 2A-2d
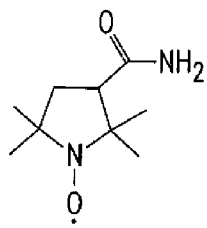 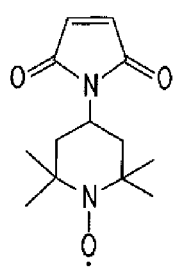 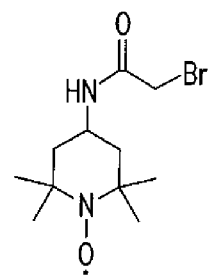
3-Carbamoyl-PROXYL, LogP=0.9
4-Maleimido-TEMPO, LogP=2.9
4-(2-Bromoacetamido)-TEMPO, LogP=1.9
FIG. 2A-2e   FIG. 2A-2f   FIG. 2A-2g

Figure 1A:
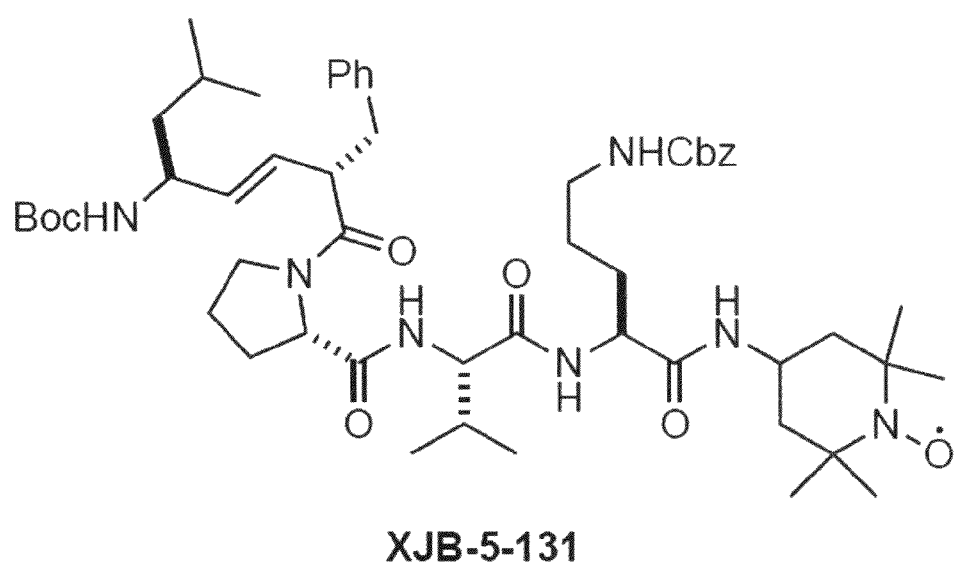
Figure 1B:
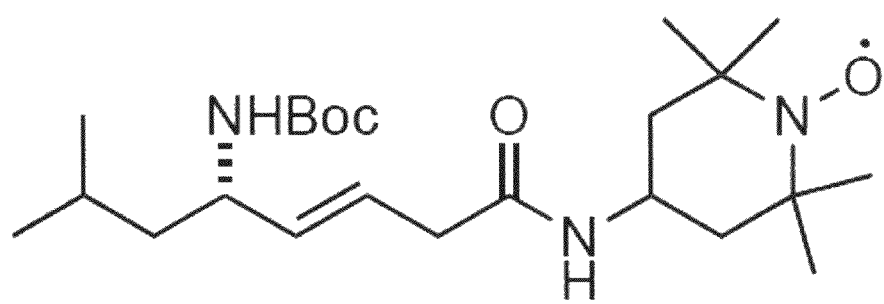
Figure 1C:
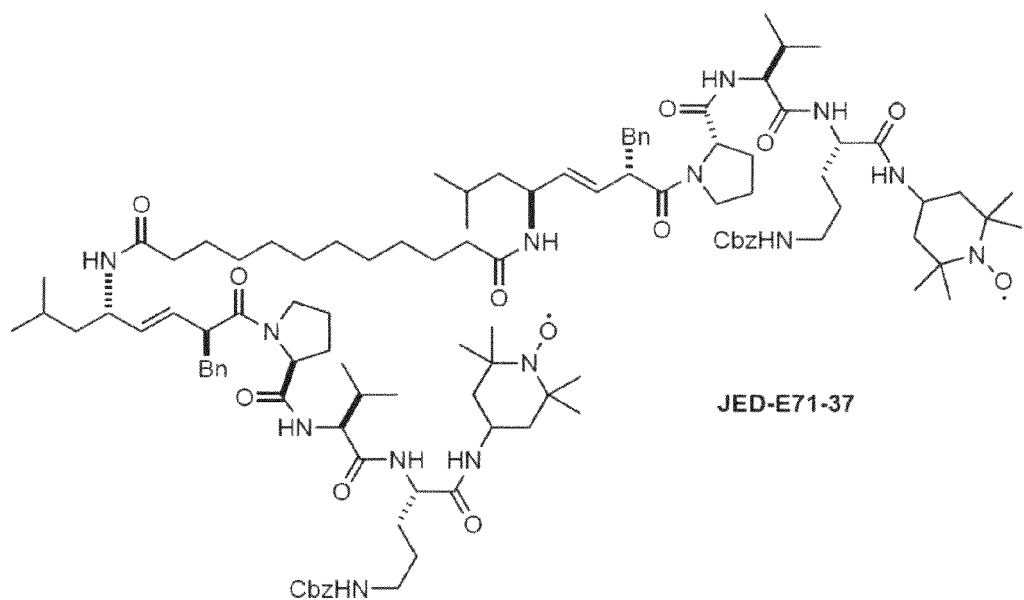
Figure 1D:
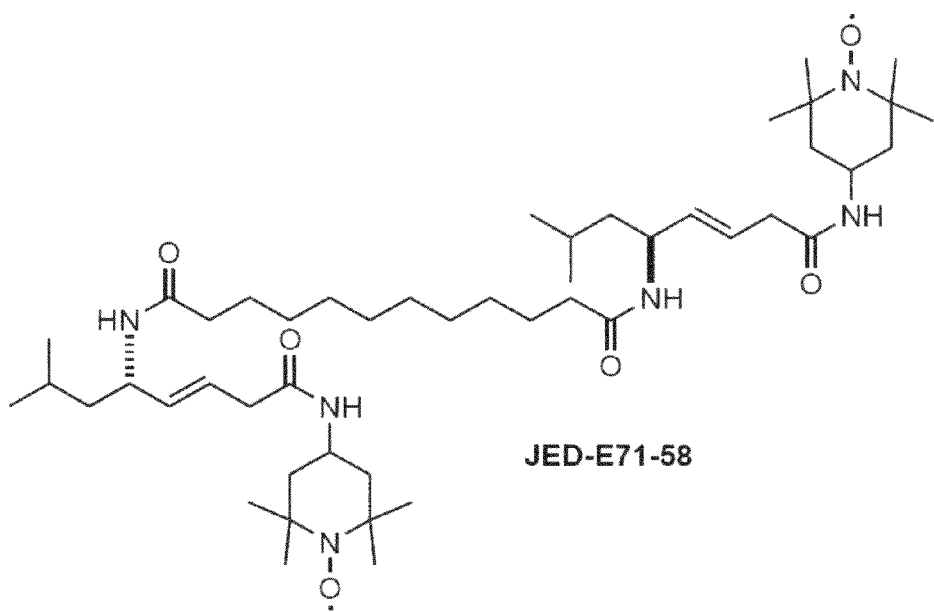
Figures 2A, 2B:
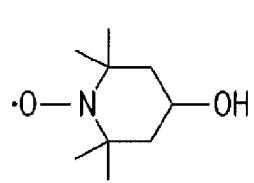
Figure 2B:
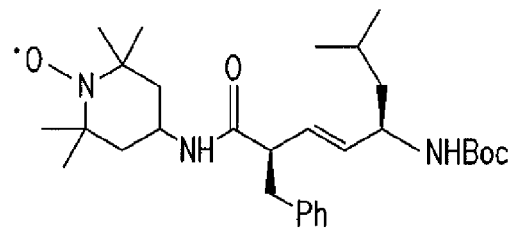

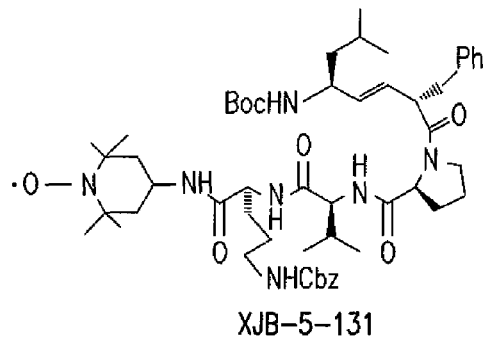
XJB-5-131
FIG. 2B-1a
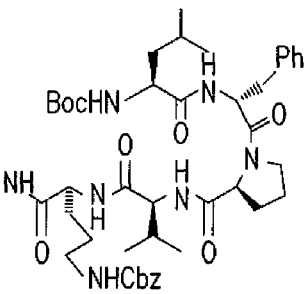
XJB-5-125
FIG. 2B-1b
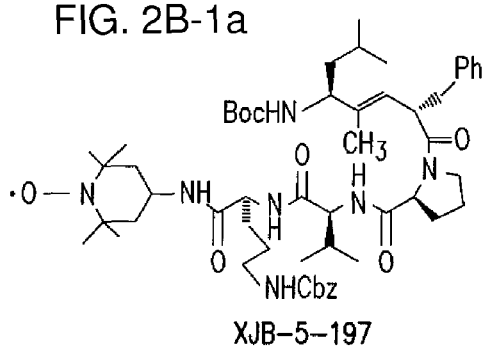
XJB-5-197
FIG. 2B-1c
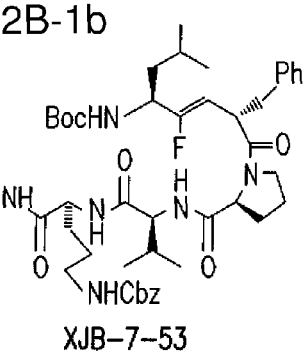
XJB-7-53
FIG. 2B-1d
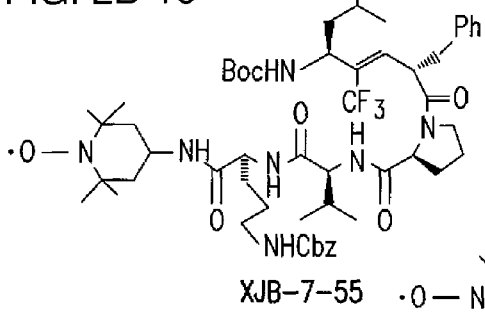
XJB-7-55
FIG. 2B-1e
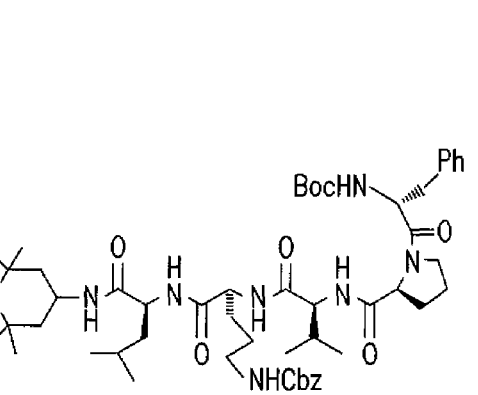
XJB-7-75  FIG. 2B-1f
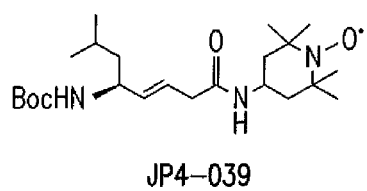
JP4-039
FIG. 2B-1g
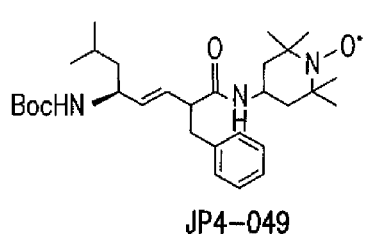
JP4-049
FIG. 2B-1h

TEMPOL

XJB-5-208

XJB-5-133

XJB-5-208

XJB-2-300

XJB-2-70

*XJB-5-194*

XJB-5-241

XJB-5-127

XJB-5-234

XJB-7-42

XJB-7-43

FIGURE 6C

| Symptom | Progeriod XPF patient | Ercc1$^{-/-}$ mice | Ercc1$^{-/\Delta}$ mice |
|---|---|---|---|
| Age at onset | 10 yr | perinatal | 6-8 weeks |
| Life span | 16 yr | 4 weeks | 28 weeks |
| hyperpigmentation | + | ? | ? |
| atrophic epidermis | + | + | ? |
| hearing loss | + | ? | ? |
| visual impairment | + | + | + |
| tremors | + | + | + |
| ataxia | + | + | + |
| cerebral atrophy | + | + | + |
| hypertension | + | ? | ? |
| renal acidosis | + | + | + |
| ↑ serum liver enzymes | + | + | + |
| ↓ serum albumin | + | + | + |
| BM degeneration | + | + | + |
| osteopenia | + | + | + |
| kyphosis | + | + | + |
| dystonia | + | + | + |
| sarcopenia | + | + | + |
| growth retardation | + | + | + |
| cachexia | + | + | + |
| aged appearance | + | + | + |
| neoplasias | - | - | - |

FIGURE 6D

| Symptom | Age at onset (weeks) |
|---|---|
| Dystonia* | 8.9 |
| Trembling* | 11.2 |
| Kyphosis | 12.9 |
| Ocular changes | 14.9 |
| Ataxia* | 15.1 |
| Muscle wasting | 15.3 |
| Priapism* | 17.1 |
| Urinary incontinence* | 19.6 |
| Reduced activity | 20.4 |

**Double Blinded twin study:
eliminates genetic and environmental variables**

FIGURE 8

Age at on set of symptoms (wks)

| Symptom | XJB | Oil | p-value | n= (XJB,oil) |
|---|---|---|---|---|
| Dystonia | 8.6* | 6.6* | 0.006 | 7,5 |
| Trembling | 9.8 | 8.0 | 0.2 | 7,5 |
| Kyphosis | 13.1 | 12.1 | 0.4 | 7,5 |
| Ataxia | 16.5* | 14.0* | 0.004 | 7,5 |
| Wasting | 16.8* | 14.8* | 0.004 | 7,5 |
| Eye | 20.2 | 14.9 | 0.08 | 2,3 |
| Priapism | N/A | 17.6 | | 0,2 |
| Lethargy | 21.6* | 17.4* | 0.04 | 4,4 |
| Incontinence | N/A | 12.4 | | 0,2 |
| Fistula | 8.0 | 10.8 | | 1,2 |
| Aging Score | 87% | 8% | <0.001 | 5,5 |

XJB-5-131 $Ercc1^{-/\Delta}$ mouse    Control (oil) $Ercc1^{-/\Delta}$ mouse

XJB-5-131 $Ercc1^{-/\Delta}$ mouse     Control (oil) $Ercc1^{-/\Delta}$ mouse

Cream Only      XJB-5-131-treated

Cream only      XJB-5-131-treated

Cream only   JP4-039-treated

COMPOUNDS FOR THE TREATMENT OF PATHOLOGIES ASSOCIATED WITH AGING AND DEGENERATIVE DISORDERS

CROSS-REFERENCE TO RELATED APPLICATION

This is a divisional of U.S. patent application Ser. No. 12/930,702, filed Jan. 14, 2011, which is a continuation of International Application No. PCT/US2009/050869, filed Jul. 16, 2009, which claims the benefit of U.S. Provisional Patent Application No. 61/081,678, filed Jul. 17, 2008, all of which are hereby incorporated by reference.

GRANT INFORMATION

This invention was made with government support under Grant No. U19A1068021 and Grant No. ES016114, both awarded by the National Institutes of Health. The government has certain rights in the invention.

1. INTRODUCTION

The present invention relates to methods for reducing and/or delaying one or more signs of aging and/or degeneration which comprise administering, to a subject in need of such treatment, one or more of the compounds as set forth herein.

2. BACKGROUND OF THE INVENTION

2.1 Aging

It is estimated that in the next 25 years, the number of individuals over the age of 65 in the United States will double (U.S. Department of Health and Human Services, 2003). With increased chronological age, there is progressive attrition of homeostatic reserve of all organ systems (Resnick and Dosa, 2004). As a consequence, aged individuals have a dramatically increased risk of numerous debilitating diseases including bone fractures, cardiovascular disease, cognitive impairment, diabetes and cancer (Resnick and Dosa, 2004). Therefore, as American demographics shift, increasing demands are placed on our health care system (Crippen, 2000). Identifying strategies to prevent or delay age-associated frailty and diseases is imperative for maintaining the health of our population as well as our nation's economy.

The molecular basis of the progressive loss of homeostatic reserve with aging is controversial (Kirkwood, 2005b; Resnick and Dosa, 2004). There is strong evidence that genetics contribute significantly to lifespan and end-of-life fitness (Hekimi and Guarente, 2003). This was demonstrated by identifying single genes that when mutated or overexpressed attenuate and extend lifespan, respectively (Kurosu et al., 2005). Many of the genes that regulate lifespan affect the growth hormone (GH)/insulin-like growth factor 1 (IGF1) axis, which controls cellular proliferation and growth (Kenyon, 2005). Suppression of this axis extends lifespan significantly and delays age-related diseases (Bartke, 2005).

Alternatively, the disposable soma theory of aging posits that aging is the consequence of accumulation of stochastic molecular and cellular damage (Kirkwood, 2005b). The precise nature of the damage that is responsible for aging-related degenerative changes remains ill-defined, but may include mitochondrial damage, telomere attrition, nuclear dysmorphology, accumulation of genetic mutations, DNA, protein or membrane damage.

There are several lines of evidence to support the notion that DNA damage is one type of molecular damage that contributes to aging. At the forefront of this is the observation that the majority of human progerias (or syndromes of accelerated aging) are caused by inherited mutations in genes required for genome maintenance, including Werner syndrome, Cockayne syndrome, trichothiodystrophy and ataxia telangiectasia (Hasty et al., 2003). Furthermore both DNA lesions (Hamilton et al., 2001) and genetic mutations caused by DNA damage (Dolle et al., 2002) accumulate in tissues with aging. Finally, mice harboring germ-line mutations that confer resistance to genotoxic stress are long-lived (Maier et al., 2004; Migliaccio et al., 1999).

ERCC1-XPF is a highly conserved structure-specific endonuclease that is required for at least two DNA repair mechanisms in mammalian cells: nucleotide excision repair (Sijbers et al., 1996) and DNA interstrand crosslink repair (Niedernhofer et al., 2004). Genetic deletion of either Ercc1 or Xpf in the mouse causes an identical and very severe phenotype (McWhir et al., 1993; Tian et al., 2004; Weeda et al., 1997). Embryonic development of null mice is normal, but postnatally they develop numerous symptoms associated with advanced age including epidermal atrophy and hyperpigmentation, visual impairment, cerebral atrophy with cognitive deficits, cerebellar degeneration, hypertension, renal insufficiency, decreased liver function, anemia and bone marrow degeneration, osteoporosis, sarcopenia, cachexia, and decreased lifespan (Niedernhofer et al., 2006; Prasher et al., 2005; Weeda et al., 1997, and see International Patent Application Publication No. WO2006/052136).

To determine if this progeroid phenotype had commonalities with the natural aging process, the transcriptome from the liver of Ercc1$^{-/-}$ mice was compared to that of old wild type mice and a highly significant correlation was identified (Niedernhofer et al., 2006). Similar expression changes were also identified in young wild type mice after chronic exposure to a DNA damaging agent. This provides direct experimental evidence that DNA damage induces changes that mimic aging at the fundamental level of gene expression.

Gene ontology classification of the expression data was used to predict pathophysiologic changes that were similar in Ercc1$^{-/-}$ mice and old wild type mice (Niedernhofer et al., 2006). These predictions were tested comparing Ercc1$^{-/-}$ mice, young and old wild type mice. For all predictions tested, Ercc1$^{-/-}$ were more similar to old mice than to their wild type littermates despite the vast difference in age (3 weeks vs. 120 weeks). Both Ercc1$^{-/-}$ and old mice displayed hyposomatotropism, hepatic accumulation of glycogen and triglycerides, decreased bone density, increased peroxisome biogenesis, increased apoptosis and decreased cellular proliferation. Therefore, Ercc1$^{-/-}$ and old mice share not only broad changes in gene expression, but also endocrine, metabolic and cell signaling changes. This implies that ERCC1-deficient mice are an accurate and rapid model system for studying systemic aging in mammals. A case of human progeria caused by ERCC1-XPF deficiency with symptoms near-identical to those observed in ERCC1-deficient mice has been reported (Niedernhofer et al., 2006). Therefore function of ERCC1-XPF is conserved from man to mouse and the discovery of what is driving aging-like degenerative changes in ERCC1-deficient mice will have direct implications for human health.

A number of the degenerative changes associated with normal aging may be manifested in an accelerated form and/or in younger individuals. Examples of such degenerative disorders include neurodegenerative disorders such as Alzheimer's disease, Huntington's disease, Parkinson's disease and osteoporosis, and joint degenerative conditions such as osteoarthritis, rheumatoid arthritis and intervertebral disc degeneration.

2.2 Free Radicals, Aging and Degeneration

Cells undergo some degree of oxidative stress by way of generating reactive oxygen species ("ROS") and reactive nitrogen species ("RNS"). Specifically, the cellular respiration pathway generates ROS and RNS within the mitochondrial membrane of the cell (Kelso et al., 2001). Reactive oxygen species include free radicals, reactive anions containing oxygen atoms, and molecules containing oxygen atoms that can either produce free radicals or are chemically activated by them. Specific examples include superoxide anion, hydroxyl radical, and hydroperoxides.

Naturally occurring enzymes, such as superoxide dismutase ("SOD") and catalase, detoxify ROS and RNS radicals to allow normal metabolic activity to occur. Significant deviations from cell homeostasis, such as hemorrhagic shock, lead to an oxidative stress state, thereby causing "electron leakage" from the mitochondrial membrane. This "electron leakage" produces an excess amount of ROS for which the cell's natural antioxidants cannot compensate. Specifically, SOD cannot accommodate the excess production of ROS associated with hemorrhagic shock which ultimately leads to premature mitochondria dysfunction and cell death via apoptosis (Kentner et al., 2002).

Cardiolipin ("CL") is an anionic phospholipid exclusively found in the inner mitochondrial membrane of eukaryotic cells (Iverson and Orrenius, 2002). Under normal conditions, the pro-apoptotic protein cytochrome C is anchored to the mitochondrial inner membrane by binding with CL (Tuominen, et al., 2002). The acyl moieties of CL are susceptible to peroxidation by reactive oxygen species. When ROS are generated within mitochondria in excess quantities, cytochrome C bound to CL can function as an oxidase and induces extensive peroxidation of CL in the mitochondrial membrane (Kagan et al., 2005a and 2005b).

The peroxidation of the CL weakens the binding between the CL and cytochrome C (Shidoji, et al., 1999). This leads to the release of the cytochrome C into the mitochondrial intermembrane space, inducing apoptotic cell death. Further, the peroxidation of CL has the effect of opening the mitochondrial permeability transition pore ("MPTP"; Dolder et al., 2001; Imai et al., 2003). Accordingly, the mitochondrial membrane swells and releases the cytochrome C into the cytosol. Excess cytochrome C in the cytosol leads to cellular apoptosis (Iverson et al., 2003).

Moreover, mitochondrial dysfunction and cell death may ultimately lead to multiple organ failure despite resuscitative efforts or supplemental oxygen supply (Cairns, 2001). Reduction of oxidative stress delays, even inhibits, physiological conditions that otherwise might occur, such as hypoxia.

One of the limitations of SOD is that it cannot easily penetrate the cell membrane. However, nitroxide radicals, such as TEMPO (2,2,6,6-tetramethylpiperidine-N-oxyl) and its derivatives, have been shown to penetrate the cell membrane better than SOD and inhibit the formation of ROS, particularly superoxide, due to their reduction by the mitochondrial electron transport chain to hydroxyl amine radical scavengers (Wipf et al., 2005a).

Examples of antioxidant agents include agents set forth in US 2007161544 and US2007161573, such as, for example, XJB-5-131.

The aging-related and degenerative changes described above are associated with deterioration in the context of impaired regenerative capacity. There appears to be an inverse relationship between the maximum lifespan of a species and the amount of ROS and RNS that species produces (Finkel, 2000). Caloric restriction, which reduces ROS and RNS production, promotes longevity and delays the onset of age-related diseases (Heilbronn, 2003). Thus, effective ROS and RNS scavengers are potential therapeutic agents for age-related pathologies and degenerative conditions.

3. SUMMARY OF THE INVENTION

The present invention relates to methods for reducing and/or delaying one or more signs of aging and/or the progression of a degenerative disorder comprising administering, to a subject in need of such treatment, a compound as disclosed herein according to Formula 1, 2 or 3, below, including, but not limited to, a compound which comprises a TEMPO or 4-amino-TEMPOL functional group, such as, but not limited to, XJB-5-131, JP4-039, JED-E71-37 or JED-E71-58 (see FIG. 1A-D for chemical structures of these latter compounds). The invention is based, at least in part, on (i) the discovery that treatment with the 4-amino-TEMPOL containing compound XJB-5-131 inhibited the development of various indicia of senescence and degeneration in vivo in a murine model of aging, Ercc1$^{-/\Delta}$ mice; (ii) the discovery that 4-amino-TEMPOL containing JP4-039 reduced cellular senescence in vitro (iii) the discovery that two compounds which each contain two 4-amino-TEMPOL groups, JED-E71-37 and JED-E71-58, reduced oxidation-related cell damage in vitro and epidermal atrophy in vivo; and (iv) the discovery that XJB-5-131 delayed progression of symptoms in an animal model of Huntington's disease.

4. BRIEF DESCRIPTION OF THE FIGURES

FIG. 1A-D. Structures of (A) XJB-5-131; (B) JP4-039; (C) JED-E71-37; and (D) JED-E71-58.

FIG. 2A-D. Compounds as set forth herein. (2A-1$a$-2A-2$g$) Non-limiting examples of certain nitrodes. The log P values were estimated using the online calculator of molecular properties and drug likeness on the Molinspirations Web site (www.molinspiration.com/cgibin/properties). TIPNO is "tert-butyl isopropyl phenyl nitroxide." (2B-1$a$-2B-3$f$) Examples of structures of certain compounds as set forth herein, and the structure of TEMPOL. (C) Example of a synthetic pathway for the TEMPO-hemigramicidin conjugates. (D) Schematic of a synthesis protocol for JP4-039.

Figures 2B, 2C:
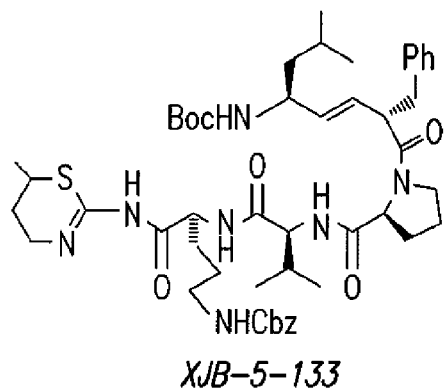
Figures 2B, 2C, 2D:
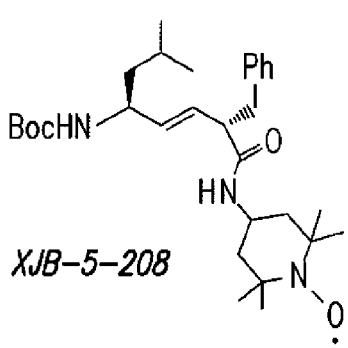
Figures 2B, 2C, 2D, 2E:
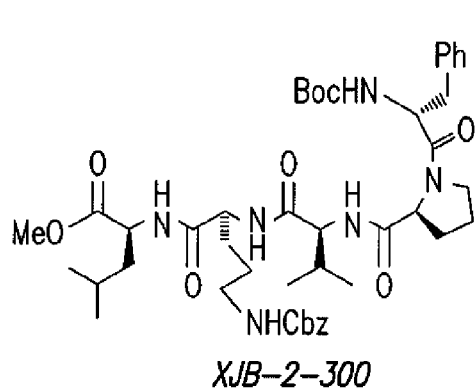
Figures 2B, 2C, 2D, 2E, 2F:
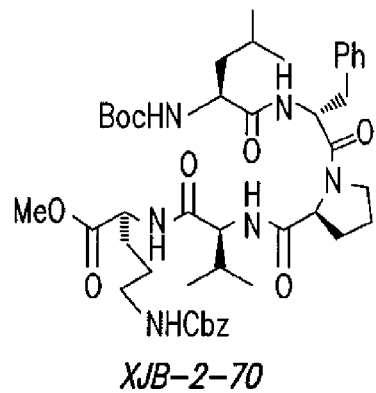
Figures 2, 2B, 3, 3A:
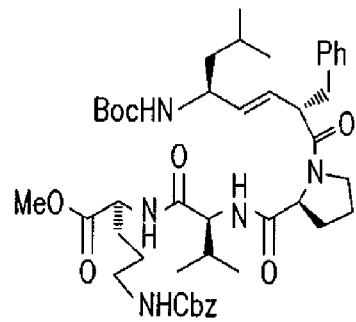
Figures 2, 2B, 3, 3B:
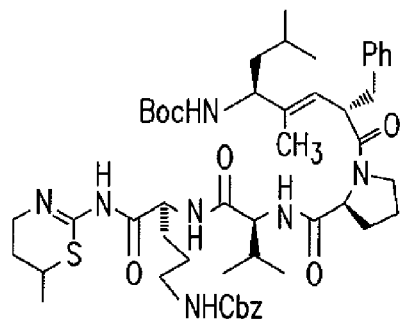
Figures 2, 2B, 3, 3C:
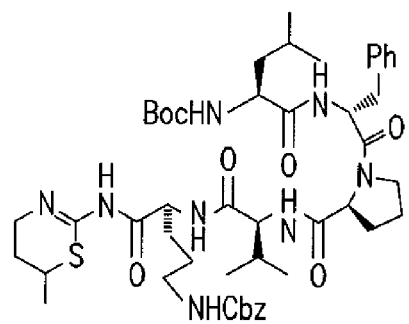
Figures 2, 2B, 3, 3D:
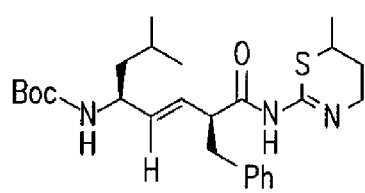
Figures 2, 2B, 3, 3E:
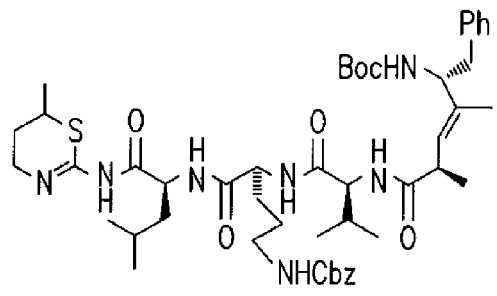
Figures 2, 2B, 3, 3F:
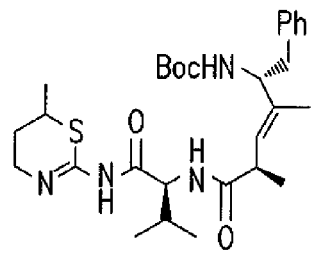
Figure 2C:
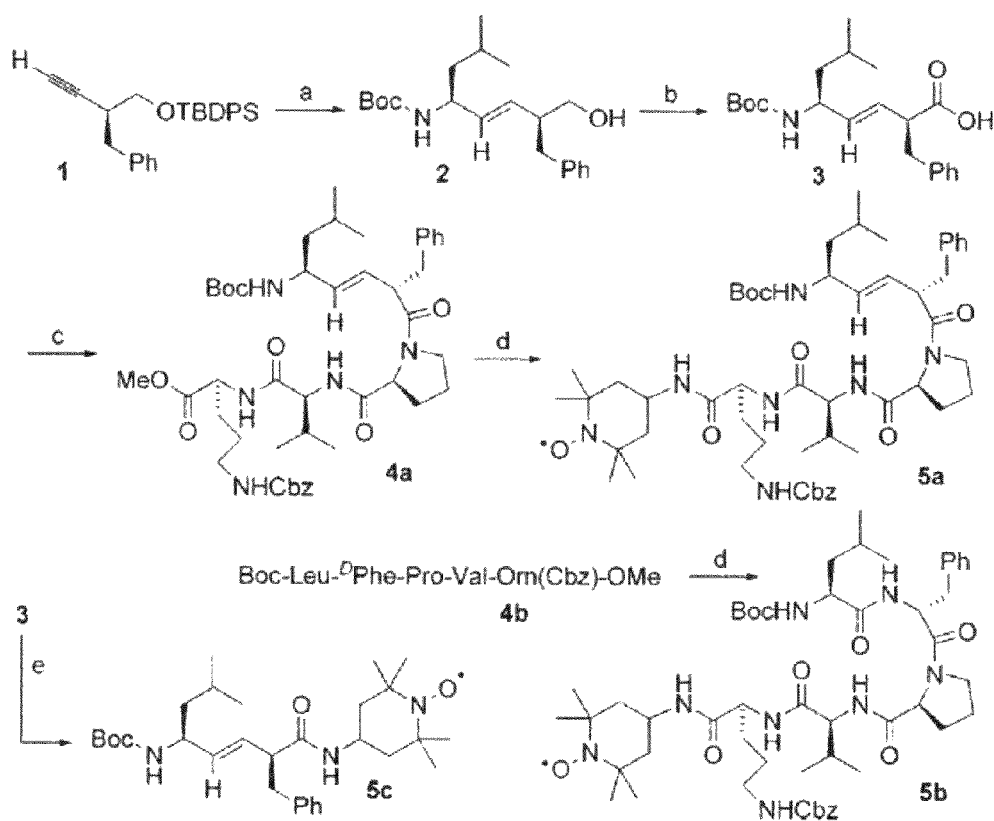
Figure 2D:
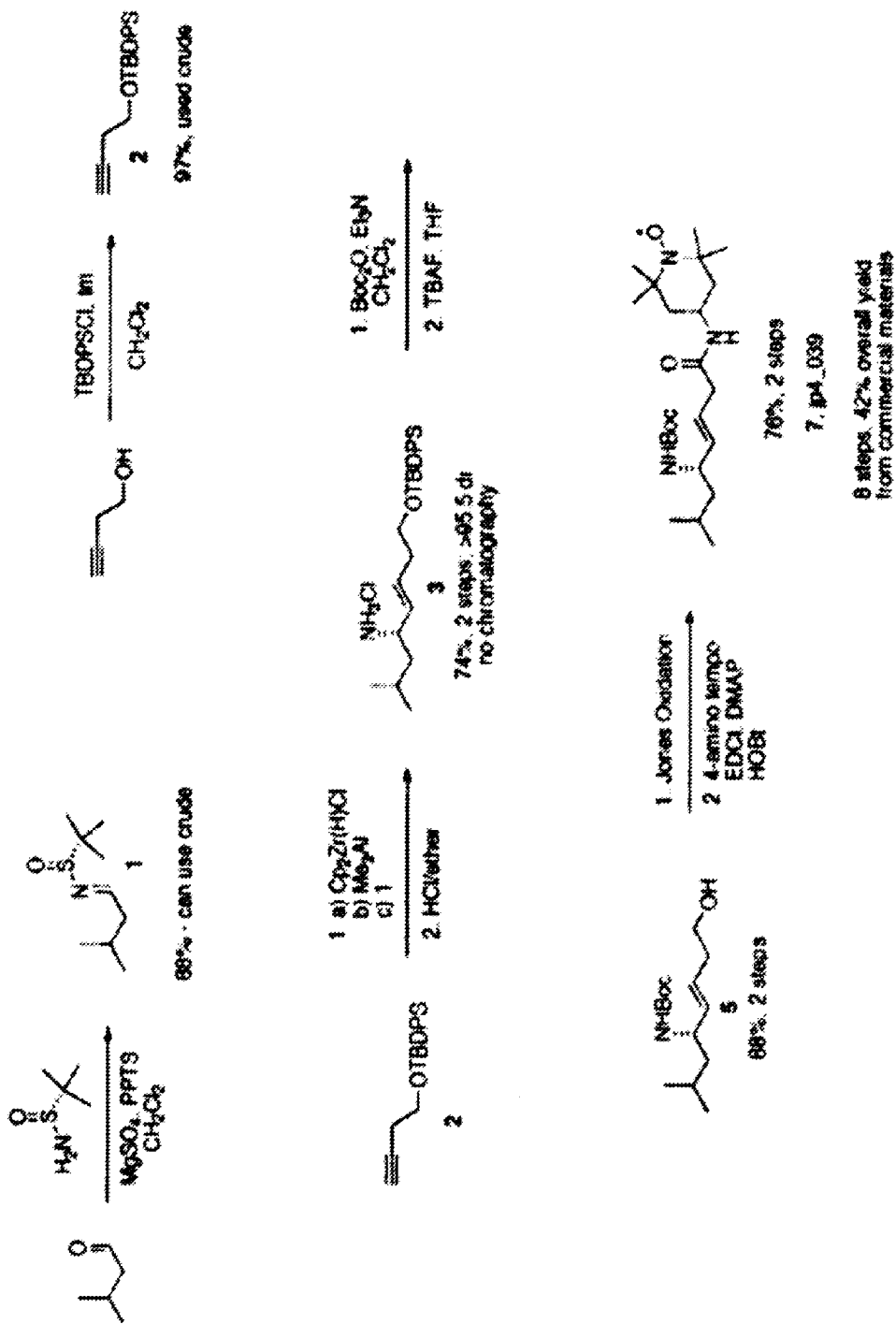
Figure 3:
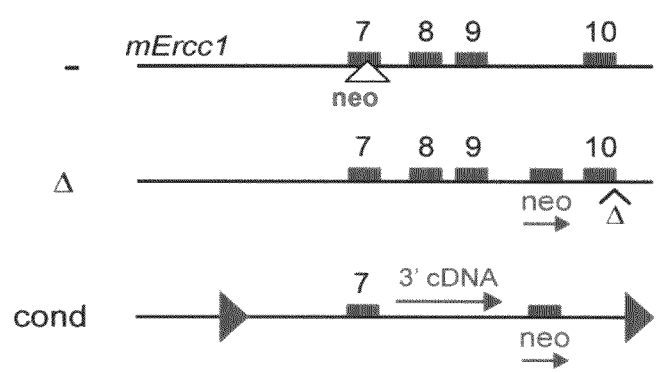

FIG. 3. Schematic diagram of mErcc1 targeting constructs. In the knock-out allele (−) exon 7 was interrupted with a neomycin selectable marker. In the hypomorphic allele (Δ), a 7 amino acid deletion was placed at the C-terminus of the protein to humanize the gene and a neo cassette in intron 9, which attenuated expression of Ercc1. In the conditional allele (cond), exon 7 was fused with the cDNA of exons 8-10 and the entire region floxed with loxP sites recognized by Cre-recombinase, allowing tissue-specific deletion of ERCC1, for example in the skin (see FIG. 10).

Figure 4:
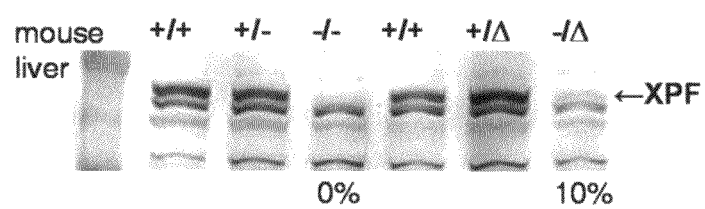

FIG. 4. Immunodetection of XPF, the obligate binding partner of ERCC1, in protein extracts isolated from the liver of Ercc1 mutant mice. The genotype of the mice is indicated above the lanes. Below the blots are indicated the calculated level of XPF expression in the Ercc1 mutant mice, relative to wild type (100%).

Figure 5:
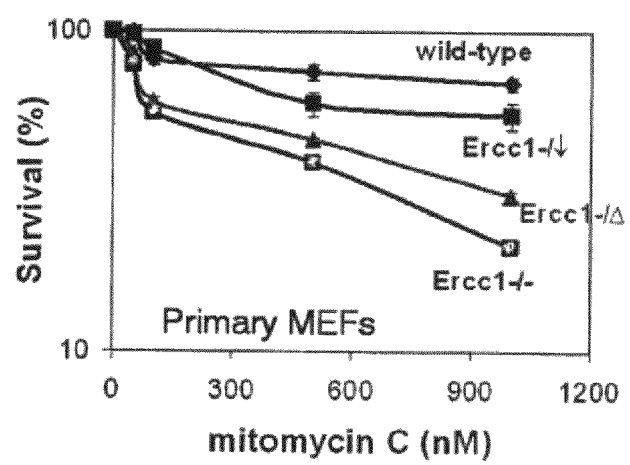

FIG. 5. Clonogenic survival assay measuring the sensitivity of ERCC1-deficient cells to the DNA damaging agent mitomycin C. Wild-type data is represented by a circle; Ercc1$^{-/+}$ by a square; Ercc1$^{-/\Delta}$ by a triangle, and Erccr1$^{-/-}$ by an open square.

Figure 6A:
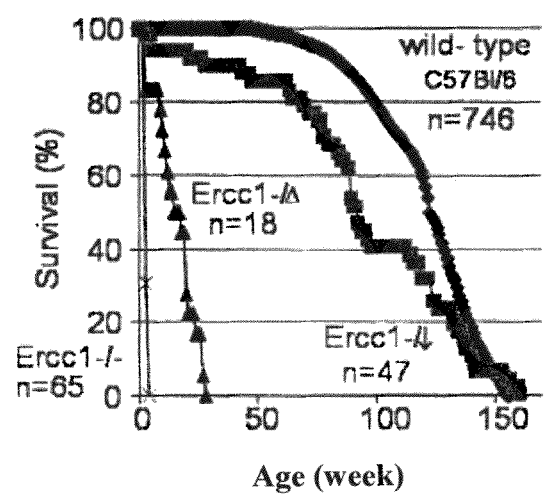

FIGS. 6 A-D. (A) Lifespan of mice expressing various levels of ERCC1-XPF compared to wild type C57B1/6 mice (100%; adapted from (Rowlatt et al., 1976). Wild-type data is represented by a diamond; Ercc1$^{-/\Delta}$ by a square; Ercc1$^{-/\Delta}$ by a triangle, and Erccr1$^{-/-}$ by crosses. (B) The spontaneous premature aging phenotype of Ercc1$^{-/\Delta}$ mice. The mice were healthy for the first 8-9 weeks of life then began to display progressive symptoms associated with aging. These included dystonia, trembling, weight loss, proximal muscle wasting, kyphosis, ataxia, loss of vision and hearing, impaired kidney and liver function and urinary incontinence. Histopathologic analysis and microCT revealed osteoporosis, intervertebral disc degeneration, bone marrow hypoplasia, epidermal atrophy and neurodegeneration. The maximum lifespan was seven months. (C) Clinical features of progeria caused by mutation of XPF and progeroid mice due to mutation of Ercc1. (D) Age at onset of progeroid symptoms in Ercc1$^{-/\Delta}$ mice as determined from a cumulative history of examining >60 mice. Symptoms marked with an asterisk indicate symptoms caused by neurodegeneration.

Figure 7:
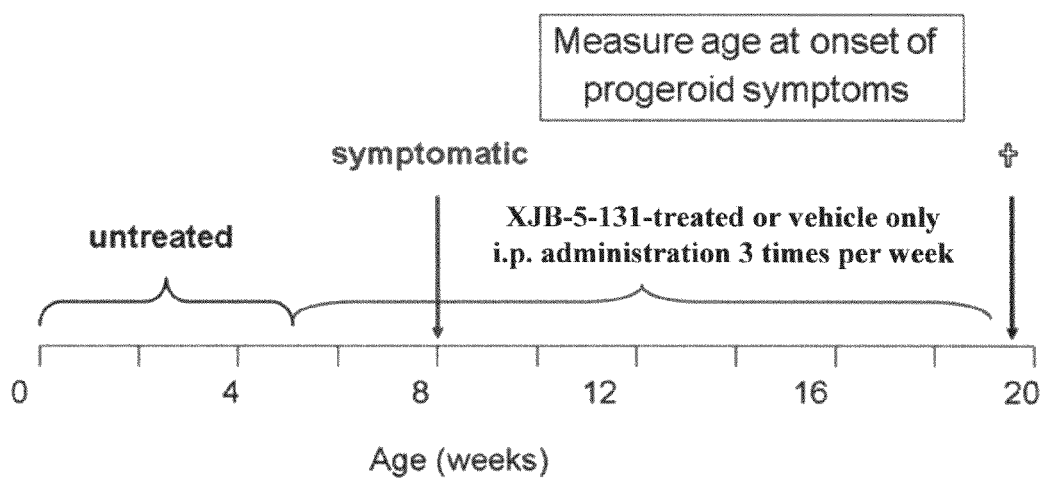

FIG. 7. Experimental system for determining the impact of a therapeutic compound on the healthspan of Ercc1$^{-/\Delta}$ mice with accelerated aging. Transgenic mice or mutant animals were born from heterozygous crossings. Only litters with two Ercc1$^{-/\Delta}$ mice were enrolled in the study so that siblings could be used to assess the effect of a therapeutic compound, XJB-5-131 vs. vehicle in a pair-wise comparison. Treatments were initiated before the mice became symptomatic. The age at onset of progeroid symptoms were measured biweekly by an investigator blinded to the treatment of the mice.

FIG. 8. Summary table showing the age at onset of progeroid symptoms in Ercc1$^{-/\Delta}$ mice treated with XJB-5-131 or vehicle only. Treating Ercc1$^{-/\Delta}$ mice with one example of the compounds as disclosed herein, XJB-5-131, delayed the onset of progeroid symptoms and aging pathologies. Values marked with an asterisk indicate a symptom of accelerated aging that was significantly delayed (including dystonia, ataxia, muscle wasting and decreased spontaneous activity or lethargy). The aging score reflected the relative age at onset of all progeroid symptoms in a mouse treated with XJB-5-131 vs. its sibling treated with oil only and was thus a measure of healthspan.

FIG. 9A-D. (A) Comparison of sibling Ercc1$^{-/\Delta}$ mice treated with XJB-5-131 or vehicle only (sunflower seed oil) according to the protocol shown in FIG. 7. The duration of treatment of mice in this figure was three times per week beginning at 5 weeks of age and continuing throughout their lifespan. The mouse treated with XJB-5-131 had less: (1) neurodegeneration seen as a normal reflex (splaying of the hind limbs rather than clasping) upon tail suspension; (2) muscle wasting in the hind quarters and (3) improved general appearance (bottom panel). (B) Bar graph showing glycosaminoglycan content of intervertebral discs of Ercc1$^{-/\Delta}$ mice either treated with XJB-5-131 or vehicle (sunflower seed oil) according to the protocol shown in FIG. 7. The duration of treatment of mice in this figure was three times per week beginning at 5 weeks of age and continuing throughout their lifespan. (C) Decreased neurodegeneration in the cerebellum of a mouse treated with XJB-5-131 compared to a sibling Ercc1$^{-/\Delta}$ mouse that was treated with vehicle only (oil). Neurodegeneration was detected by immunostaining for glial acidic fibrillary protein (GFAP; brown staining). (D) Preservation of insulin-producing β-islet cells (patches of pale purple highlighted with arrows) in the pancreas of an XJB-5-131-treated mouse. Pancreatic sections were stained with haematoxylin and eosin.

FIG. 10A-D. (A) Effects of (photo)aging in Ercc1$^{-/\Delta}$ mice either treated with XJB-5-131 (80 μg emulsified in a topical cream) or cream only according to the protocol shown in FIG. 7. The duration of treatment of mice in this figure was daily for five days post-UV irradiation. (B) Compounds as disclosed herein protect skin from photoaging by improving keratin production. Skin of Ercc1$^{-/cond}$; K14-Cre mice (missing ERCC1-XPF expression only in the skin) were treated with 20 J/m2 (half of the minimal erythemal dose) five times per week for 10 weeks to induce photoaging of the skin. Immediately after UV exposure, XJB-5-131 was applied (80 μg in 50 μL of cream) using a cotton applicator. Twenty-four hours after the last treatment, mice were euthanized and skin harvested for histopathologic examination. Skin sections were immunostained for keratin (red), DNA to reveal nuclei (blue) and actin (green). (C) Compounds as disclosed herein protect skin from inflammation in response to ultraviolet radiation. Skin of Ercc1$^{-/cond}$; K14-Cre mice (missing ERCC1-XPF expression only in the skin) were treated with 500 J/m2 (12.5×the minimal erythemal dose) to induce erythema. Immediately after UV exposure, XJB-5-131 was applied (80 μg in 50 μL of cream) using a cotton applicator. Twenty-four hours after treatment, mice were euthanized and skin harvested for histopathologic examination. Skin sections were immunostained for keratin (red), DNA to reveal nuclei (blue) and actin (green). The thickness of the epidermal layer (indicated by the white bracket) is less in mice treated with XJB-5-131 than in mice treated with cream alone. (D) Compounds as disclosed herein reduce epidermal atrophy. Old (>24 months) normal mice were shaved and their skin treated with JP4-039 (450 μg in 50 μL of cream) or vehicle (cream) only five times per week for 10 weeks. Twenty-four hours after the last treatment, mice were euthanized and skin harvested for histopathologic examination. Skin sections were stained for DNA to reveal nuclei (blue) and actin (green). The thickness of the epidermal layer (indicated by the bracket) was significantly greater in mice treated with JP4-039 than in mice treated with vehicle (cream) alone, demonstrating preservation of skin thickness or reversal of epidermal atrophy, a common age-associated feature.

Figure 11A:
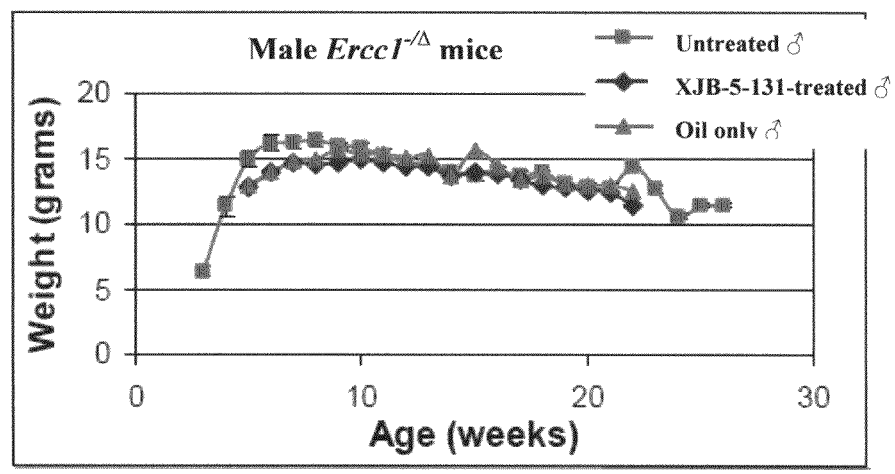
Figure 11B:
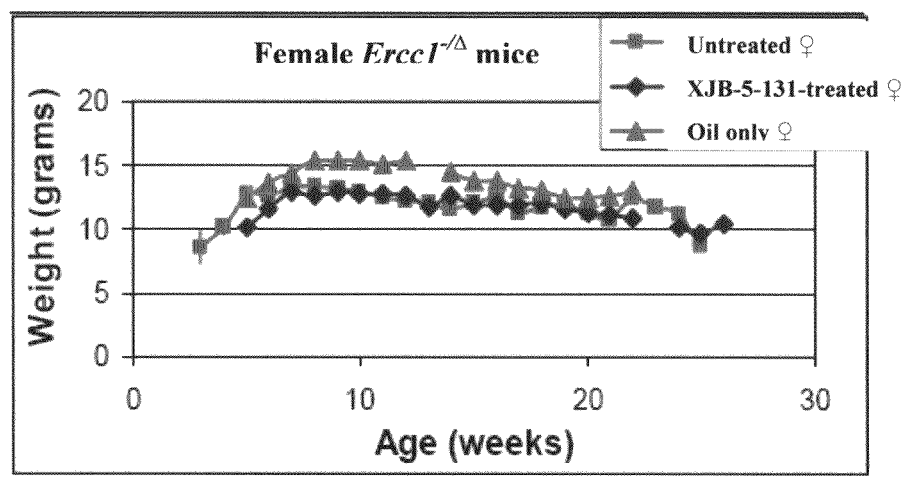

FIG. 11A-B. Weights as a function of age of (A) male and (B) female Ercc1$^{-/\Delta}$ mice either treated with XJB-5-131 or vehicle (sunflower seed oil) according to the protocol shown in FIG. 7.

Figure 12:
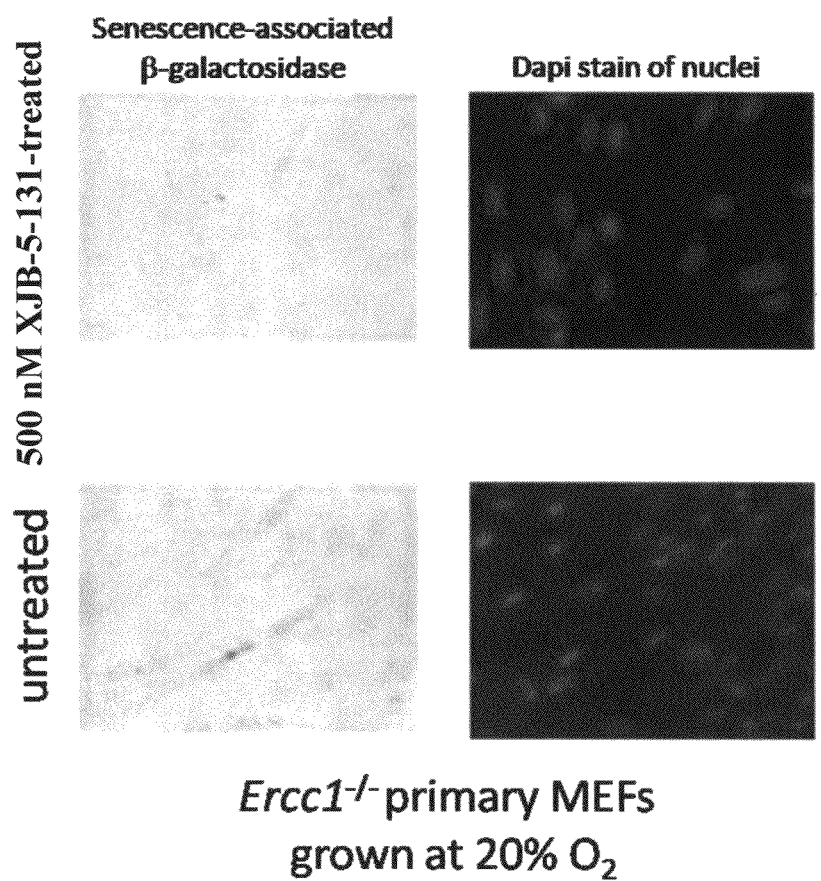

FIG. 12. SA-β galactosidase (a marker of cellular senescence) staining in mouse embryonic fibroblast ("MEF") cells prepared from Ercc1$^{-/-}$ mice, where the MEF cells were either treated with XJB-5-131 (500 μm dissolved in media) or media alone continuously for 48 hours prior to fixing and staining the cells.

Figure 13A:
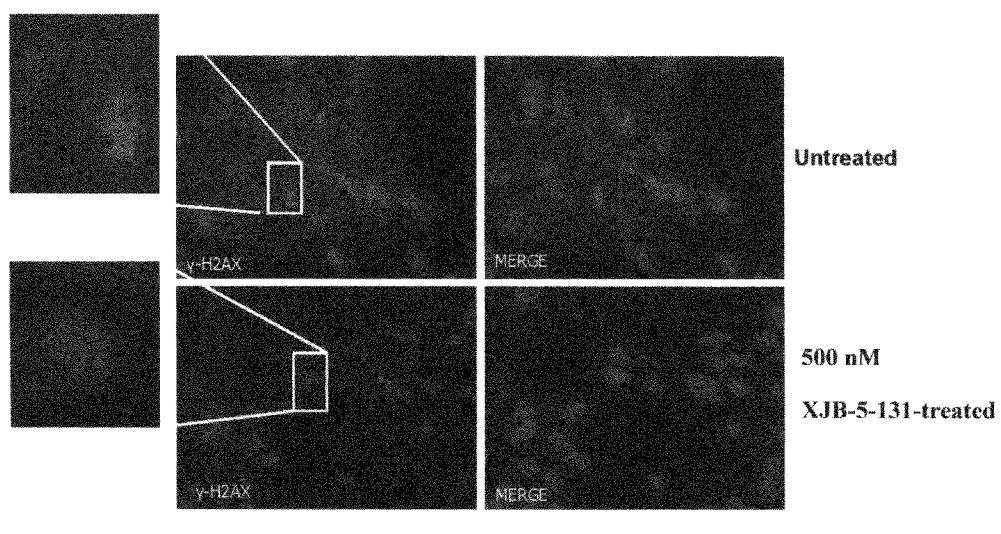
Figure 13B:
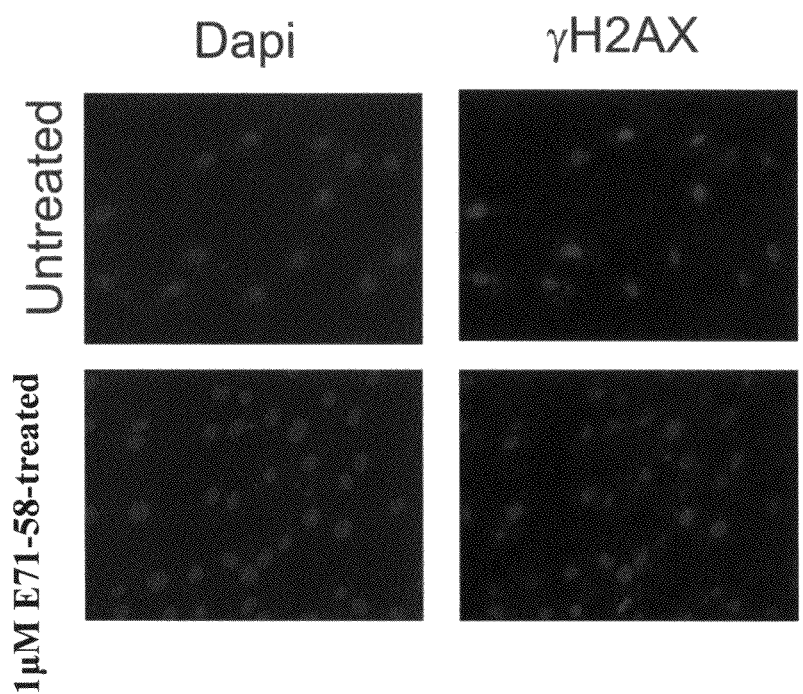

FIG. 13A-B. γH2AX immunostaining of Ercc1$^{-/-}$ primary MEF grown at 20% oxygen to induce oxidative stress. Phosphorylated H2AX (γH2AX is a marker of cellular senescence and DNA damage. The MEF cells were either treated with XJB-5-131 (A) or E71-58 (B), fewer cells stained positively for γH2AX.

Figure 14:
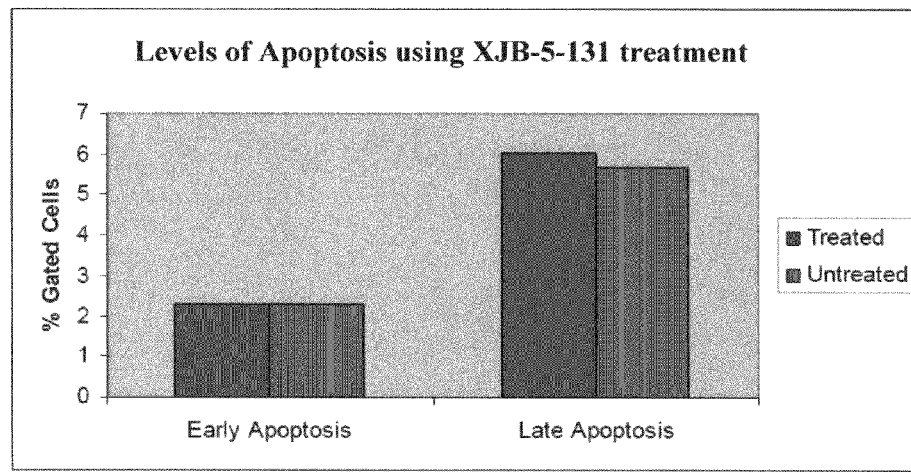

FIG. 14. Apoptosis in MEF cells prepared from Ercc1$^{-/-}$ mice, where the MEF cells were either treated with XJB-5-131 (500 nM dissolved in media) or media alone continuously for 48 hours prior to fixing and staining the cells.

Figure 15:
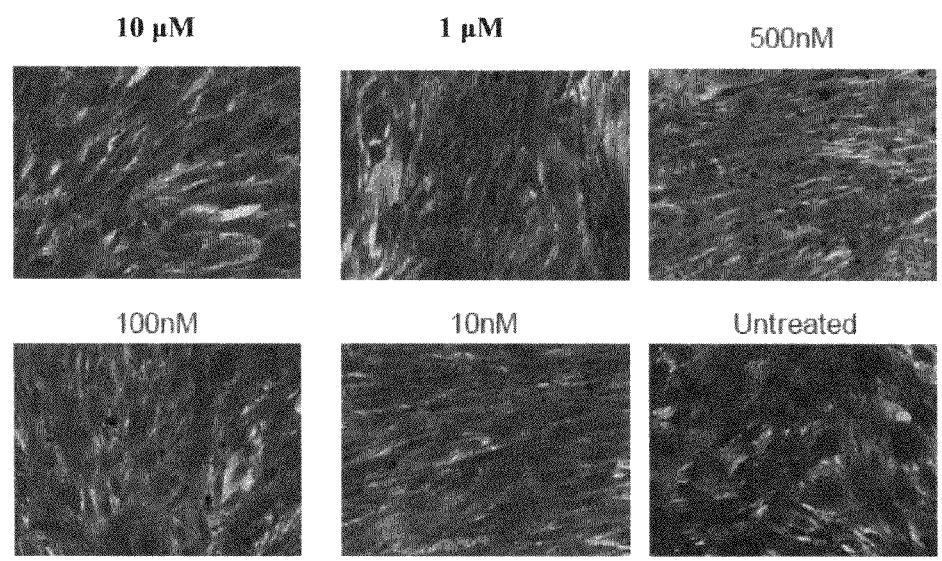

FIG. 15. Effects of varying doses of JP4-039, on proliferation and growth of MEF cells prepared from Ercc1$^{-/-}$ mice. JP4-039 was not toxic to cells at concentrations as high as 10 μM.

Figure 16:
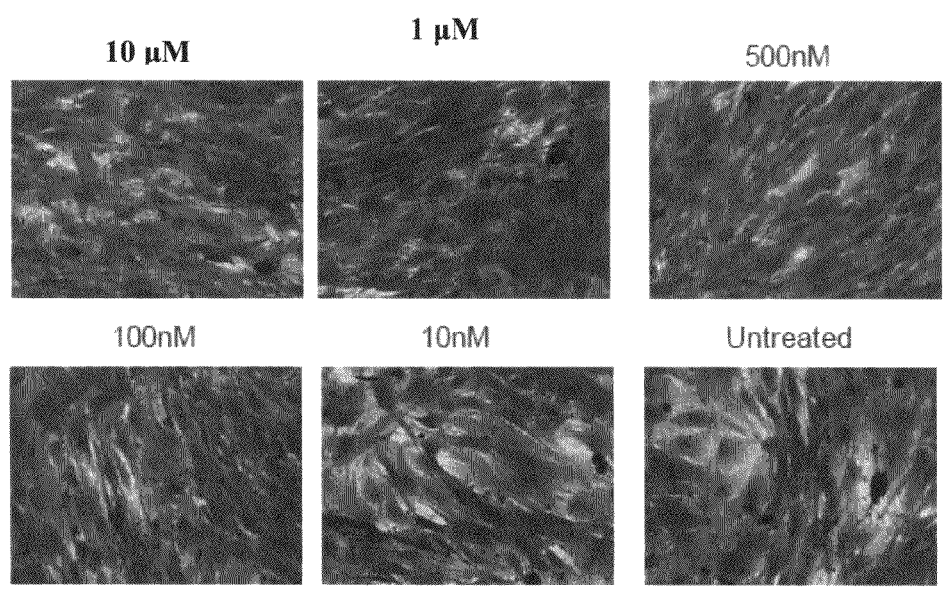

FIG. 16. Effects of varying doses of JP4-039, on proliferation and growth of MEF cells prepared from wild-type mice.

Figure 17:
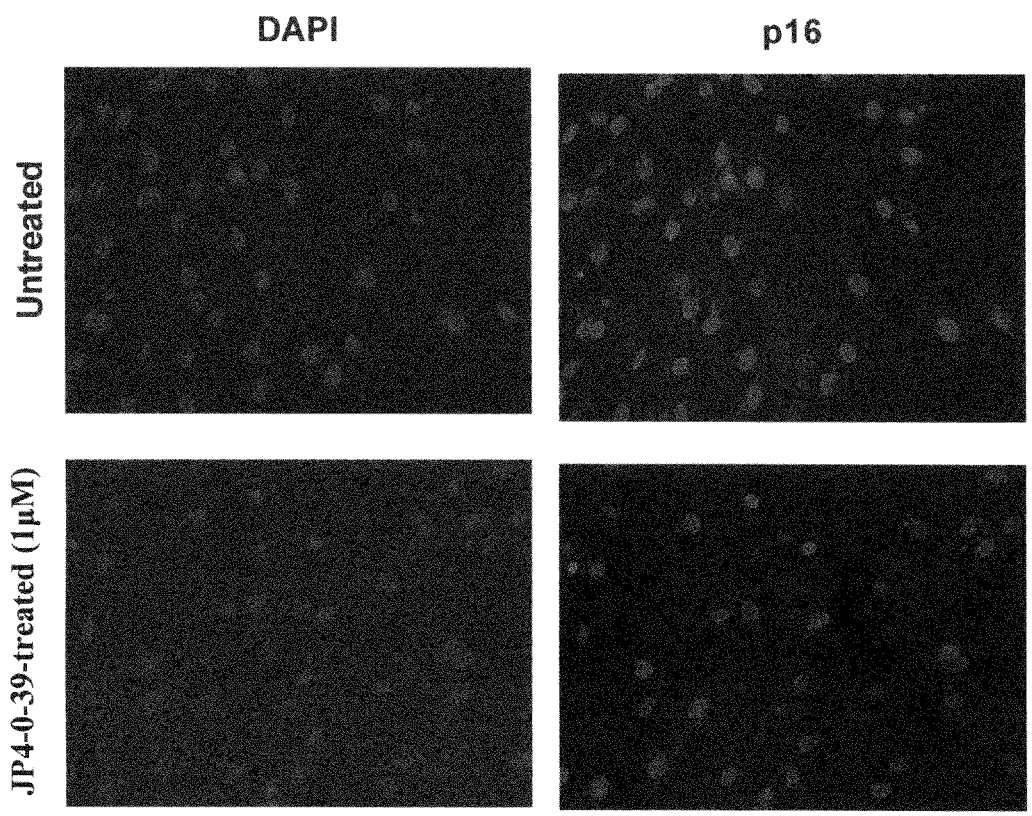

FIG. 17. Levels of p16, a marker of irreversible cellular senescence, in MEF cells prepared from Ercc1$^{-/-}$ mice, where the MEF cells were either treated with JP4-039 (10 μM dissolved in media) or media alone for 48 hours prior to fixing and immunostaining of cells.

Figure 18:
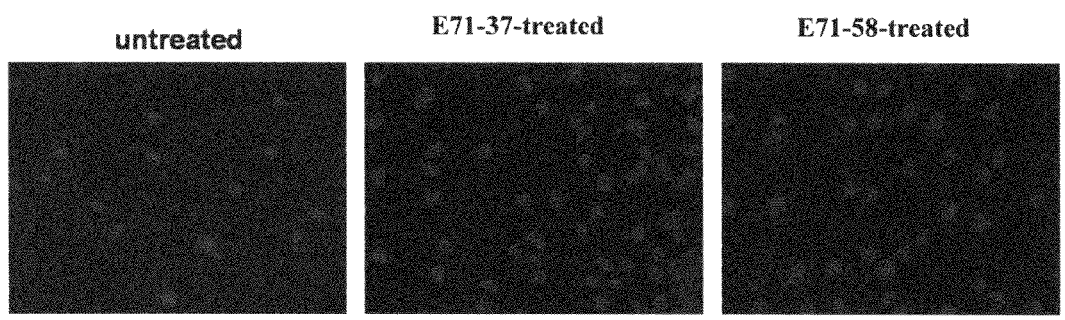

FIG. 18. Cell proliferation of primary MEF cells prepared from Ercc1$^{-/-}$ mice and grown in conditions of oxidative stress, where the MEF cells were either treated with JED-E71-37, JED-E71-58, (91 μM dissolved in media) or media alone for 48 hours prior to fixing and staining the cells.

Figure 19:
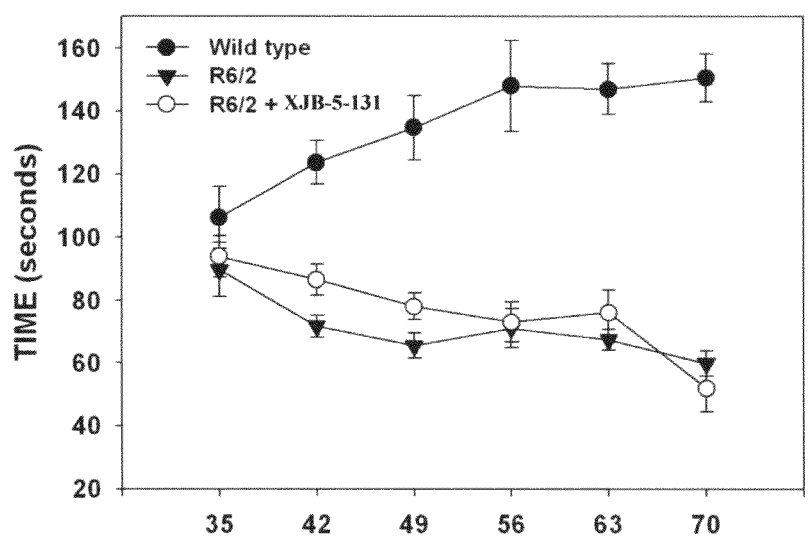

FIG. 19. XJB-5-131 preserved motor function in a mouse model of Huntington's disease. Five R6/2 mice, which model Huntington's disease, were treated three times per week with 2 mg/kg XJB-5-131 beginning at 5 weeks of life according to the scheme in FIG. 7. Motor function was assessed weekly by measuring the time animals were able to remain balanced on a rotarod, according to standard methods. Mice treated with XJB-5-131 performed significantly better at six and seven weeks of age, demonstrating that XJB-5-131 delayed the progression of symptoms of Huntington's disease.

5. DETAILED DESCRIPTION OF THE INVENTION

For clarity of presentation, and not by way of limitation, the detailed description of the invention is divided into the following subsections:
(i) compounds;
(ii) signs of aging that may be modulated; and
(iii) methods of treatment.

5.1 Compounds

The present invention provides for the use of any of a number of compounds as set forth herein, used alone or in combination. The present invention further provides for pharmaceutical compositions comprising said compounds, where a pharmaceutical composition comprises an amount of a compound effective in reducing and/or delaying one sign of aging and/or degeneration, in a suitable pharmaceutical carrier.

Whilst we are not bound by any theory, the compounds set forth herein include antioxidant compounds, free radical scavengers, and in particular, mitochondrial targeted free radical scavengers. A compound as disclosed herein according to Formula 1, 2, or 3, below, includes, but is not limited to, a compound which comprises a TEMPO or 4-amino-TEMPOL functional group, such as, but not limited to, XJB-5-131, JP4-039, JED-E71-37 or JED-E71-58.

An antioxidant compound as that term is used herein, is a compound that decreases the rate of oxidation of another compound or that inhibits or prevents reaction between a substance and oxygen or an oxygen containing compound. A compound may be determined to be an antioxidant compound by assessing its ability to decrease molecular oxidation and/or cellular sequellae of oxidative stress, for example, but not by way of limitation, the ability to decrease lipid peroxidation and/or decrease oxidative damage to protein or nucleic acid. Preferably, an antioxidant of the invention has a level of antioxidant activity between 0.01 and 1000 times the antioxidant activity of ascorbic acid in at least one assay that measures antioxidant activity.

Free radical scavengers used herein are compounds that react with free radicals. Free radical scavengers reduce free radical-induced damage, and protect against the indirect effects of free radicals produced by ionizing radiation, etc.

In one non-limiting embodiment, the compound has the structure:

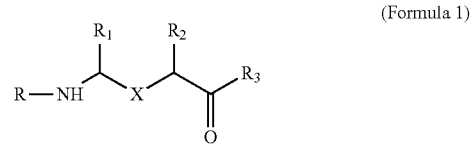

(Formula 1)

wherein X is one of and

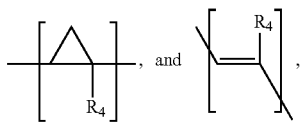

$R_1$, $R_2$ and $R_4$ are, independently, $C_1$-$C_6$ straight or branched-chain alkyl, optionally including a phenyl ($C_6H_5$) group, that optionally is methyl-, hydroxyl- or fluoro-substituted, including including: methyl, ethyl, propyl, 2-propyl, butyl, t-butyl, pentyl, hexyl, benzyl, hydroxybenzyl (e.g., 4-hydroxybenzyl), phenyl and hydroxyphenyl. $R_3$ is —NH—$R_5$, —O—$R_5$ or —CH$_2$—$R_5$, and $R_5$ is an —N—O. or —N—OH containing group. R is —C(O)—$R_6$ or —C(O)O—$R_6$, and $R_6$ is $C_1$-$C_6$ straight or branched-chain alkyl optionally comprising one or more phenyl (—$C_6H_5$) groups, and that optionally are methyl-, ethyl-, hydroxyl- or fluoro-substituted, including Boc (R=-C(O)O-tert-butyl) and Cbz (R=-C(O)O-benzyl (Bn)) groups. Excluded from this is the enantiomer XJB-5-208. As used herein, unless indicated otherwise, for instance in a structure, all compounds and/or structures described herein comprise all possible stereoisomers, individually or mixtures thereof.

As indicated above, $R_5$ is an —N—O. or —N—OH containing group. As is known to one ordinarily skilled in the art, nitroxide and nitroxide derivatives, including TEMPOL and associated TEMPO derivatives are stable radicals that can withstand biological environments. Therefore, the presence of the 4-amino-TEMPO, TEMPOL or another nitroxide "payload" within the mitochondria membrane can serve as an effective and efficient electron scavenger of the ROS being produced within the membrane. Non-limiting examples of this include TEMPO (2,2,6,6-Tetramethyl-4-piperindine 1-oxyl) and TEMPOL (4-Hydroxy-TEMPO), in which, when incorporated into the compound described herein, form, for example, when $R_3$ is —NH—$R_5$, —O—$R_5$:

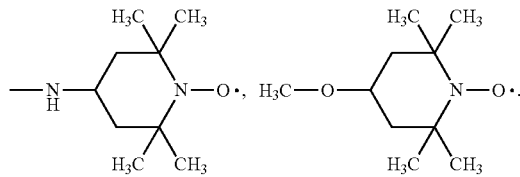

Additional non-limiting examples of —N—O. or —N—OH containing group are provided in Table 1 and in FIG. 2A (from Jiang, et al., 2007). A person of ordinary skill in the art would be able to conjugate (covalently attach) any of these compounds to the rest of the compound using common linkers and/or conjugation chemistries, such as the chemistries described herein. Table 1 provides a non-limiting excerpt from a list of over 300 identified commercially-available —N—O. or —N—OH containing compounds that may be useful in preparation of the compounds or compositions described herein.

TABLE 1

Commercially-available N—O• or N=O containing groups

| Structure | Name | CAS No. |
|---|---|---|
| 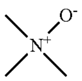 | Trimethylamine N-Oxide | 1184-78-7 |
| 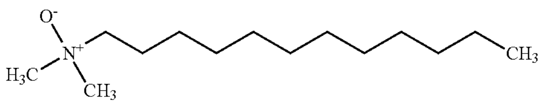 [SMILES: CCCCCCCCCCCC[N+](C)(C)[O-]] | N,N-Dimethyldodecylamine N-Oxide | 1643-20-5<br>70592-80-2 |
| 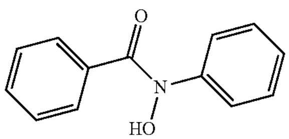 [SMILES: O=C(c1ccccc1)N(O)c1ccccc1] | N-Benzoyl-N-Phenylhydroxylamine | 304-88-1 |
| 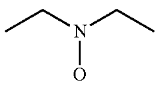 | N,N-Diethylhydroxylamine | 3710-84-7 |
| 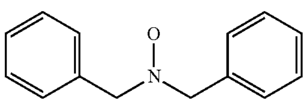 [SMILES: ON(Cc1ccccc1)Cc1ccccc1] | N,N-Dibenzylhydroxylamine | 14165-27-6<br>621-07-8 |
| 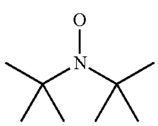 | Di-Tert-Butyl Nitroxide | 2406-25-9 |
| 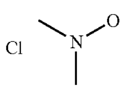 | N,N-Dimethylhydroxylamine Hydrochloride | 16645-06-0 |
| 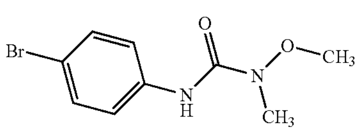 | Metobromuron | 3060-89-7 |
| 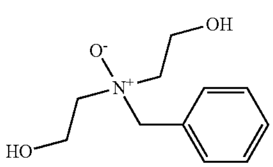 [SMILES: [O-][N+](CCO)(CCO)Cc1ccccc1] | Benzyl-Di-Beta-Hydroxy Ethylamine-N-Oxide | |
| 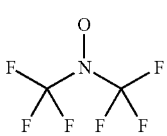 | Bis(Trifluoromethyl)Nitroxide | 2154-71-4 |
| 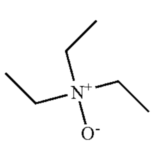 | Triethylamine N-Oxide | 2687-45-8 |

TABLE 1-continued

Commercially-available N—O• or N═O containing groups

| Structure | Name | CAS No. |
|---|---|---|
| 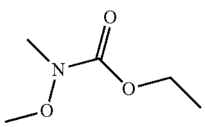 | N-Methoxy-N-Methylcarbamate | 6919-62-6 |
| | N,N-BIS(2-CHLORO-6-FLUOROBENZYL)-N-[(([2,2-DICHLORO-1-(1,4-THIAZINAN-4-YL+)ETH-YLIDENE]AMINO)CAR-BONYL)OXY]AMINE | |
| 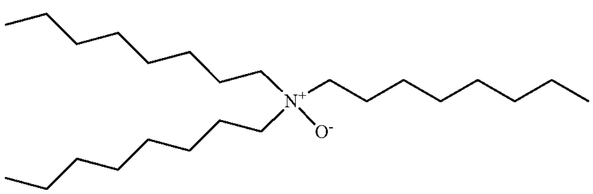 [SMILES: CCCCCCCC[N+]([O-])(CCCCCCCC)CCCCCCCC] | Tri-N-Octylamine N-Oxide | 13103-04-3 |
| | DIETHYL (N-METHOXY-N-METHYLCARBAMOYLMETH-YL)PHOSPHONATE | 124931-120 |
| | N-Methoxy-N-Methyl-2-(Triphenyl-phosphoranylidene)Acetamide | 129986-67-0 |
| 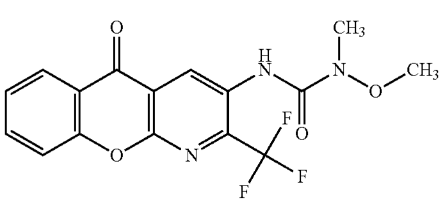 [SMILES: CON(C)C(=O)Nc1cc2c(=O)c3ccccc3oc2nc1C(F)(F)F] | N-Methoxy-N-Methyl-N'-[5-Oxo-2-(Trifluoromethyl)-5h-Chromeno[2,3-B]Pyridi+N-3-Yl]Urea | |

TABLE 1-continued

Commercially-available N—O• or N=O containing groups

| Structure | Name | CAS No. |
|---|---|---|
| 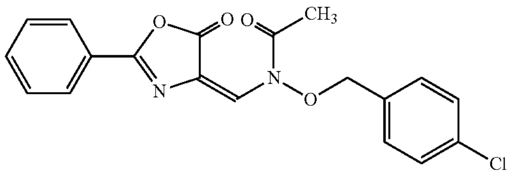 [SMILES: CC(=O)N(/C=C1/N=C(c2ccccc2)OC1=O)OCc1ccc(Cl)cc1] | N-[(4-Chlorobenzyl)Oxy]-N-([5-Oxo-2-Phenyl-1,3-Oxazol-4(5h)-Yliden]Methyl+)Acetamide | |
| 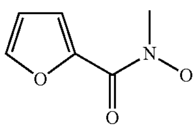 | N-Methylfurohydroxamic Acid | 109531-96-6 |
| 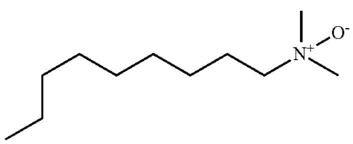 | N,N-Dimethylnonylamine N-Oxide | 2536-13-2 |
| 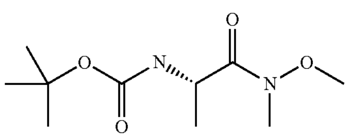 [SMILES: CON(C)C(=O)[C@H](C)NC(=O)OC(C)(C)C] | N-(Tert-Butoxycarbonyl)-L-Alanine N'-Methoxy-N'-Methylamide | 87694-49-3 |
| 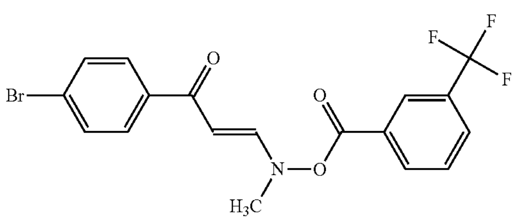 [SMILES: CN(/C=C/C(=O)c1ccc(Br)cc1)OC(=O)c1cccc(C(F)(F)F)c1] | 1-(4-Bromophenyl)-3-(Methyl([3-(Trifluoromethyl)Benzoyl]Oxy)Amino)-2-Prop+ En-1-One | |
| | 2-([[(Anilinocarbonyl)Oxy](Methyl)Amino]Methylene)-5-(4-Chlorophenyl)-1,3+-Cyclohexanedione | |
| 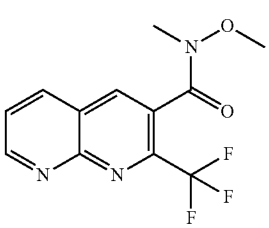 [SMILES: CON(C)C(=O)c1cc2cccnc2nc1C(F)(F)F] | N-Methoxy-N-Methyl-2-(Trifluoromethyl)-1,8-Naphthyridine-3-Carboxamide | |
| 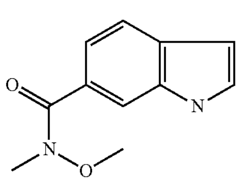 | N-Methoxy-N-Methyl-Indole-6-Carboxamide | |

TABLE 1-continued

Commercially-available N—O• or N=O containing groups

| Structure | Name | CAS No. |
|---|---|---|
| Desferrioxamin | | |
| 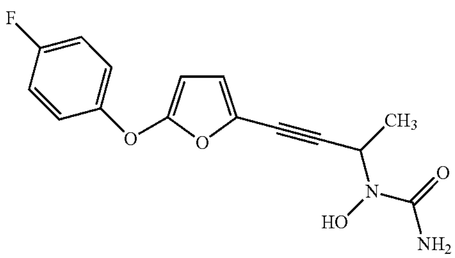 [SMILES: CC(C#Cc1ccc(Oc2ccc(F)cc2)o1)N(O)C(N)=O] | AKOS 91254 | 127408-31-5 |
| 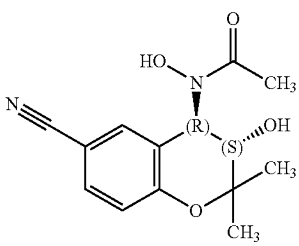 | N-[(3s,4r)-6-Cyano-3,4-Dihydro-3-Hydroxy-2,2-Dimethyl-2h-1-Benzopyran-4-Y+L]-N-Hydroxyacetamide | 127408-31-5 |
| 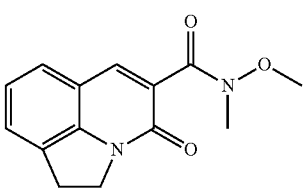 [SMILES: CON(C)C(=O)c1cc2cccc3c2n(c1=O)CC3] | N-Methoxy-N-Methyl-1,2-Dihydro-4-Oxo-Pyrrolo[3,2,1-Ij]Quinoline-5-Carboxa+Mide | |
| 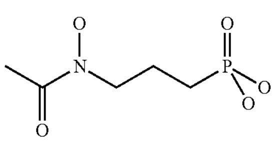 | Fr-900098 | |
| 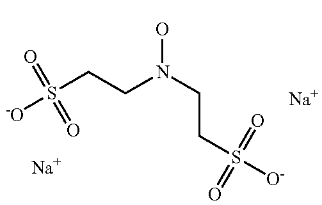 | 2,2'-(Hydroxyimino)Bis-Ethanesulfonic Acid Disodium Salt | 133986-51-3 |

TABLE 1-continued

Commercially-available N—O• or N=O containing groups

| Structure | Name | CAS No. |
|---|---|---|
| 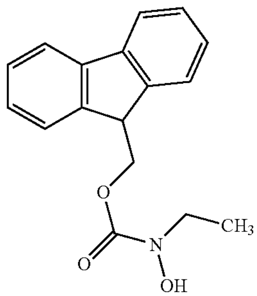 [SMILES: CCN(O)C(=O)OCC1c2ccccc2-c2ccccc21] | Fmoc-N-Ethyl-Hydroxylamine | |
| | Bis(N,N-Dimethylhydroxamido)Hydroxooxovanadate | |
| 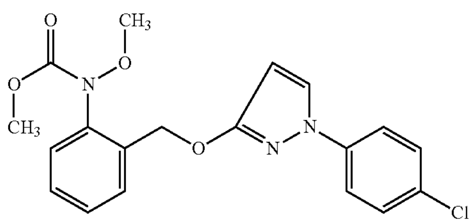 [SMILES: COC(=O)N(OC)c1ccccc1COc1ccn(-c2ccc(Cl)cc2)n1] | Pyraclostrobin | 175013-18-0 |
| 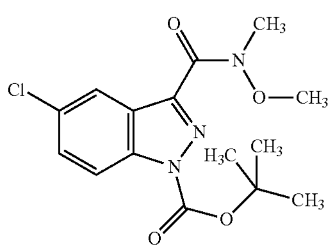 [SMILES: CON(C)C(=O)c1nn(C(=O)OC(C)(C)C)c2ccc(Cl)cc12] | 1-Boc-5-Chloro-3-(Methoxy-Methyl-Carbamoyl)Indazole | |
| 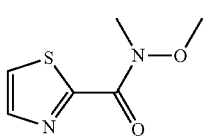 | N-Methoxy-N-Methyl-Thiazole-2-Carboxamide | |
| 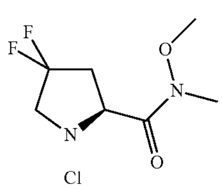 | 4,4-Difluoro-N-Methyl-N-Methoxy-L-Prolinamide Hcl | |
| | 3-Fluoro-4-(Methoxy(Methyl)Carbamoyl)Phenylboronic Acid | 913835-59-3 |

TABLE 1-continued

Commercially-available N—O• or N═O containing groups

| Structure | Name | CAS No. |
|---|---|---|
| 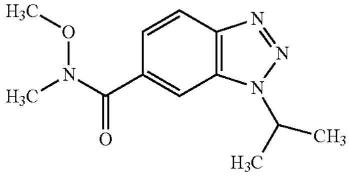 [SMILES: CON(C)C(=O)c1ccc2nnn(C(C)C)c2c1] | 1-Isopropyl-N-Methoxy-N-Methyl-1h-Benzo[D][1,2,3]Triazole-6-Carboxamide | 467235-06-9 |
| 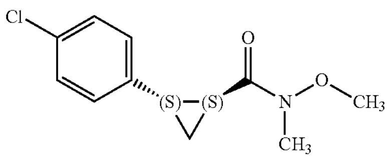 | (Trans)-2-(4-Chlorophenyl)-N-Methoxy-N-Methylcyclopropanecarboxamide | |
| 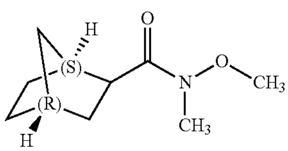 | Bicyclo[2.2.1]Heptane-2-Carboxylic Acid Methoxy-Methyl-Amide | |
| 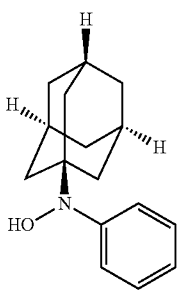 [SMILES: ON(c1ccccc1)[C@]12C[C@H]3C[C@H](C[C@H](C3)C1)C2] | Akos Bc-0582 | |
| 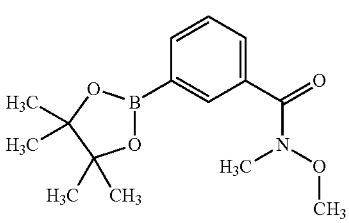 | 3-(N,O-Dimethylhydroxylaminocarbonyl)Phenylboronic Acid, Pinacol Ester | |
| 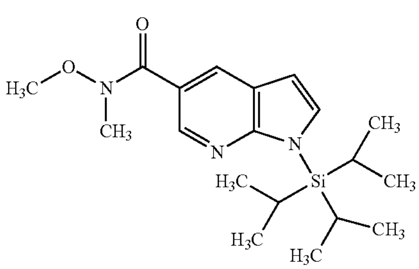 [SMILES: CON(C)C(=O)c1cnc2c(ccn2[Si](C(C)C)(C(C)C)C(C)C)c1] | 1-Triisopropylsilanyl-1h-Pyrrolo[2,3-B]Pyridine-5-Carboxylic Acid Methoxy+-Methyl-Amide | |

According to one embodiment, the compound has the structure

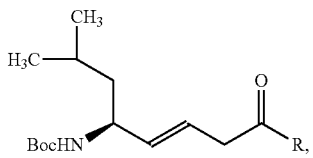

or the structure

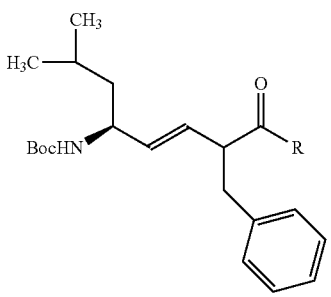

Wherein R is —NH—$R_1$, —O—$R_1$ or —$CH_2$—$R_1$, and $R_1$ is an —N—O. or —N—OH containing group. In one embodiment, R is —NH—$R_1$, and in another R is N-TEMPO.

In one non-limiting embodiment, the compound has the structure:

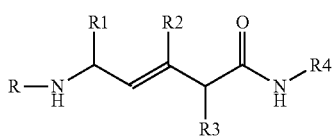

(Formula 2)

In which R1, R2 and R3 are, independently, $C_1$-$C_6$ straight or branched-chain alkyl, optionally including a phenyl ($C_6H_5$) group, that optionally is methyl-, hydroxyl- or fluoro-substituted, 2-methyl propyl, benzyl, methyl-, hydroxyl- or fluoro-substituted benzyl, such as 4-hydroxybenzyl. R4 is an —N—O. or —N—OH containing group. R is —C(O)—R5 or —C(O)O—R5, and R5 is $C_1$-$C_6$ straight or branched-chain alkyl, optionally comprising one or more phenyl (—$C_6H_5$) groups, and that optionally are methyl-, ethyl-, hydroxyl- or fluoro-substituted, including Boc and Cbz groups. In certain specific embodiments, in which R4 is TEMPO, the compound has one of the structures A, A1, A2, or A3 (Ac=Acetyl=$CH_3C(O)$—):

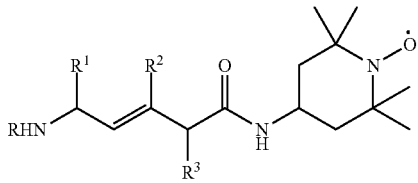

A

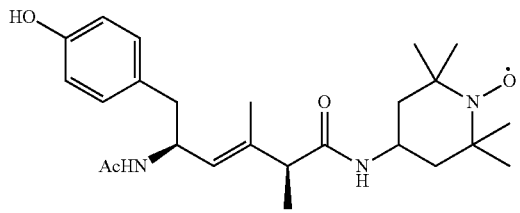

A1

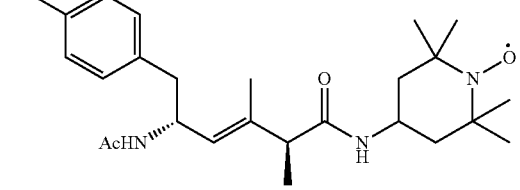

A2

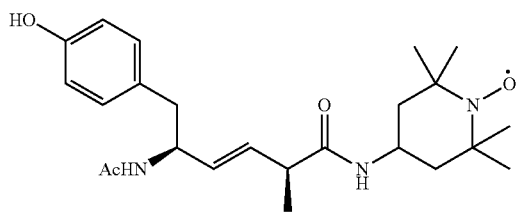

A3

In another non-limiting embodiment, the compound has the structure

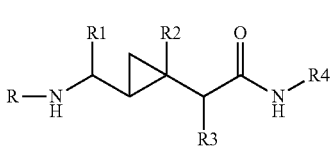

(Formula 3)

In which R1, R2 and R3 are, independently, $C_1$-$C_6$ straight or branched-chain alkyl, optionally including a phenyl ($C_6H_5$) group, that optionally is methyl-, hydroxyl- or fluoro-substituted, including 2-methyl propyl, benzyl, methyl-, hydroxyl- or fluoro-substituted benzyl, such as 4-hydroxybenzyl. R4 is an —N—O. or —N—OH containing group. R is —C(O)—R5 or —C(O)O—R5, and R5 is $C_1$-$C_6$ straight or branched-chain alkyl, optionally comprising one or more phenyl (—$C_6H_5$) groups, and that optionally are methyl-, ethyl-, hydroxyl- or fluoro-substituted, including Boc and Cbz groups. In certain specific embodiments, in which R4 is TEMPO, the compound has one of the structures D, D1, D2, or D3 (Ac=Acetyl=$CH_3C(O)$—):

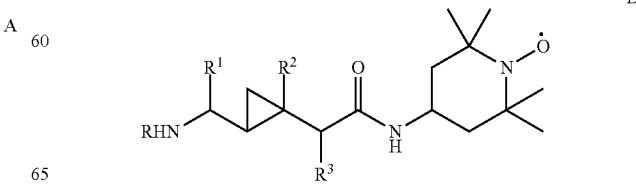

D

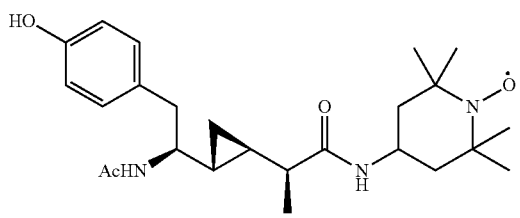
D1

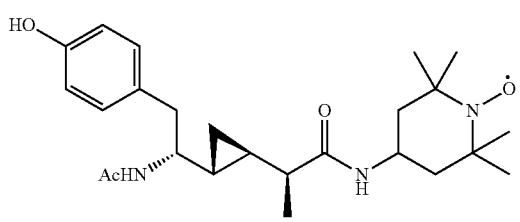
D2

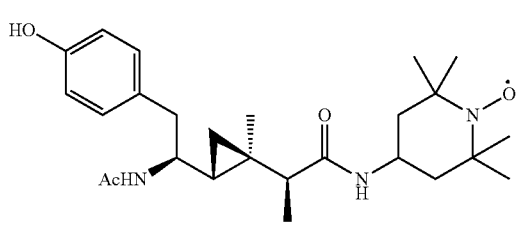
D3

The compounds described above, such as the compound of Formula 1, can be synthesized by any useful method. The compound JP4-039 may be synthesized, for example and not by limitation, by the method depicted in FIG. 2D. In one embodiment, a method of making the compounds of formula 1 is provided, and the compounds are synthesized by the following steps:

A. reacting an aldehyde of structure $R_1$—C(O)—, wherein, for example and without limitation, $R_1$ is $C_1$-$C_6$ straight or branched-chain alkyl, optionally including a phenyl ($C_6H_5$) group, that optionally is methyl-, hydroxyl- or fluoro-substituted, including: methyl, ethyl, propyl, 2-propyl, butyl, t-butyl, pentyl, hexyl, benzyl, hydroxybenzyl (e.g., 4-hydroxybenzyl), phenyl and hydroxyphenyl, with (R)-2-methylpropane-2-sulfinamide to form an imine, for example

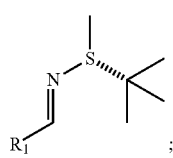
;

B. reacting a terminal alkyne-1-ol (CHC—$R_2$—C—OH), wherein, for example and without limitation, $R_2$ is not present or is branched or straight-chained alkylene, including methyl, ethyl, propyl, etc., with a tert-butyl)diphenylsilane salt to produce a t-butyldiphenyl(alkylynyloxy)silane, for example

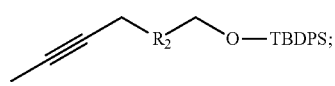

C. reacting (by hydrozirconation) the t-butyldiphenyl(alkylynyloxy)silane with the imine in the presence of an organozirconium catalyst to produce a (t-butyldiphenylsilyloxy) alkylenyl amine hydrochloride, for example

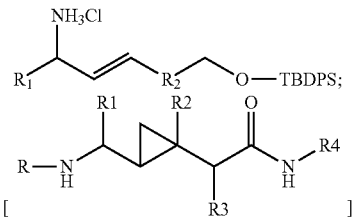

D. acylating the (t-butyldiphenylsilyloxy)alkylenyl amine hydrochloride to produce a (t-butyldiphenylsilyloxy) alkylenyl carbamate, for example

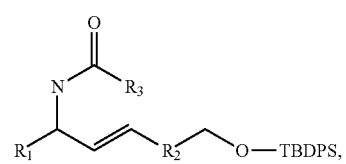

wherein, for example and without limitation, $R_3$ is $C_1$-$C_6$ straight or branched-chain alkyl, optionally including a phenyl ($C_6H_5$) group, that optionally is methyl-, hydroxyl- or fluoro-substituted, including: methyl, ethyl, propyl, 2-propyl, butyl, t-butyl, pentyl, hexyl, benzyl, hydroxybenzyl (e.g., 4-hydroxybenzyl), phenyl and hydroxyphenyl;

E. removing the t-butyldiphenylsilyl group from the (t-butyldiphenylsilyloxy)alkylenyl carbamate to produce an alkylenyl carbamate-1-ol, for example

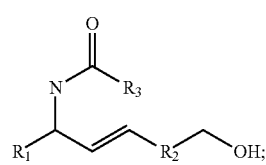

F. oxidizing the alkylenyl carbamate-1-ol to produce an alkylenyl carbamate-1-carboxylic acid, for example

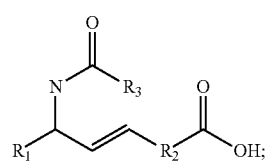

and

G. reacting alkylenyl carbamate-1-carboxylic acid with a nitroxide-containing compound comprising one of a hydroxyl or amine in a condensation reaction to produce the compound as set forth herein, for example

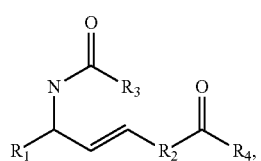

Wherein $R_4$ is —NH—$R_4$ or —O—$R_4$, and $R_4$ is an —N—O. or —N—OH containing group, such as described above.

In another non-limiting embodiment, a compound is provided having the structure R1-R2-R3 in which R1 and R3 are a group having the structure —R4-R5, in which R4 is a mitochondria targeting group and R5 is —NH—R6, —O—R6 or —CH$_2$—R6, wherein R6 is an —N—O. or —N—OH containing group, such as TEMPO. R1 and R2 may be the same or different. Likewise, R4 and R5 for each of R1 and R3 may be the same or different. R2 is a linker that, in one non-limiting embodiment, is symmetrical. FIGS. 1C and 1D depict two examples of such compounds. In one embodiment, R1 and R2 have the structure shown in formulas 1, 2, or 3, above, with all groups as defined above, including structures A, A1, A2 A3, D, D1, D2 and D3, above, an example of which is compound JED-E71-58, shown in FIG. 1D. In another embodiment, R1 and R2 are, independently, a gramicidin derivative, for example, as in the compound JED-E71-37, shown in FIG. 1C. Examples of gramicidin derivatives are provided herein, such as XJB-5-131 and XJB-5-125 (see FIG. 2B), and are further described both structurally and functionally in United States Patent Publication Nos. 20070161573 and 20070161544 as well as in Jiang, et al. 2007; Hoye, et al., 2008; and Wipf, et al., 2005a. The XJB compounds can be linked into a dimer, for example and without limitation, by reaction with the nitrogen of the BocHN groups (e.g., as in XJB-5-131), or with an amine, if present, for instance, if one or more amine groups of the compound is not acylated to form an amide (such as NHBoc or NHCbx).

In Jiang, et al., with a model of ActD-induced apoptosis in mouse embryonic cells, a library of nitroxides were screened to explore structure-activity relationships between their antioxidant/antiapoptotic properties and chemical composition and three-dimensional (3D) structure. High hydrophobicity and effective mitochondrial integration were deemed necessary but not sufficient for high antiapoptotic/antioxidant activity of a nitroxide conjugate. By designing conformationally preorganized peptidyl nitroxide conjugates and characterizing their 3D structure experimentally (circular dichroism and NMR) and theoretically (molecular dynamics), they established that the presence of the β-turn/β-sheet secondary structure is essential for the desired activity. Monte Carlo simulations in model lipid membranes confirmed that the conservation of the D-Phe-Pro reverse turn in hemi-GS analogs ensures the specific positioning of the nitroxide moiety at the mitochondrial membrane interface and maximizes their protective effects. These insights into the structure-activity relationships of nitroxide-peptide and -peptide isostere conjugates are helpful in the development of new mechanism-based therapeutically effective agents, such as those described herein.

Targeting group R4 may be a membrane active peptide fragment derived from an antibiotic molecule that acts by targeting the bacterial cell wall. Examples of such antibiotics include: bacitracins, gramicidins, valinomycins, enniatins, alamethicins, beauvericin, serratomolide, sporidesmolide, tyrocidins, polymyxins, monamycins, and lissoclinum peptides. The membrane-active peptide fragment derived from an antibiotic may include the complete antibiotic polypeptide, or portions thereof having membrane, and preferably mitochondria-targeting abilities, which is readily determined, for example, by cellular partitioning experiments using radiolabeled peptides. Examples of useful gramicidin-derived membrane active peptide fragments are the Leu-D-Phe-Pro-Val-Orn and D-Phe-Pro-Val-Orn-Leu hemigramicidin fragments. As gramicidin is circular, any hemigramicidin 5-mer is expected to be useful as a membrane active peptide fragment, including Leu-D-Phe-Pro-Val-Orn, D-Phe-Pro-Val-Orn-Leu, Pro-Val-Orn-Leu-D-Phe, Val-Orn-Leu-D-Phe-Pro and Orn-Leu-D-Phe-Pro-Val (from Gramicidin S). Any larger or smaller fragment of gramicidin, or even larger fragments containing repeated gramicidin sequences (e.g., Leu-D-Phe-Pro-Val-Orn-Leu-D-Phe-Pro-Val-Orn-Leu-D-Phe-Pro) are expected to be useful for membrane targeting, and can readily tested for such activity. In one embodiment, the Gramicidin S-derived peptide comprises a β-turn, which appears to confer to the peptide a high affinity for mitochondria. Derivatives of Gramicidin, or other antibiotic fragments, include isosteres (molecules or ions with the same number of atoms and the same number of valence electrons—as a result, they can exhibit similar pharmacokinetic and pharmacodynamic properties), such as (E)-alkene isosteres (see, United States Patent Publication Nos. 20070161573 and 20070161544 for exemplary synthesis methods). As with Gramicidin, the structure (amino acid sequence) of bacitracins, other gramicidins, valinomycins, enniatins, alamethicins, beauvericin, serratomolide, sporidesmolide, tyrocidins, polymyxins, monamycins, and lissoclinum peptides are all known, and fragments of these can be readily prepared and their membrane-targeting abilities can easily be confirmed by a person of ordinary skill in the art.

Alkene isosteres such as (E)-alkene isosteres of Gramicidin S (i.e., hemigramicidin) were used as part of the targeting sequence. See FIG. 2C for a synthetic pathway for (E)-alkene isosteres and reference number 2 for the corresponding chemical structure. First, hydrozirconation of alkyne (FIG. 2C, compound 1) with Cp$_2$ZrHCl is followed by transmetalation to Me$_2$Zn and the addition of N-Boc-isovaleraldimine. The resulting compound was then worked up using a solution of tetrabutylammonium fluoride ("TBAF") and diethyl ether with a 74% yield. The resulting compound was then treated with acetic anhydride, triethylamine (TEA), and 4-N,N'-(dimethylamino) pyridine ("DMAP") to provide a mixture of diastereomeric allylic amides with a 94% yield which was separated by chromatography. Finally, the product was worked up with K$_2$CO$_3$ in methanol to yield the (E)-alkene, depicted as compound 2. The (E)-alkene, depicted as compound 2 of FIG. 2C, was then oxidized in a multi-step process to yield the compound 3 (FIG. 2C)—an example of the (E)-alkene isostere.

The compound 3 of FIG. 2C was then conjugated with the peptide H-Pro-Val-Orn (Cbz)-OMe using 1-ethyl-3-(3-dimethylaminopropyl carbodimide hydrochloride) (EDC) as a coupling agent. The peptide is an example of a suitable targeting sequence having affinity for the mitochondria of a cell. The resulting product is shown as compound 4a in FIG. 2C. Saponification of compound 4a followed by coupling with 4-amino-TEMPO (4-AT) afforded the resulting conjugate shown as compound 5a in FIG. 2C in which the Leu-$^D$Phe peptide bond has been replaced with an (E)-alkene.

In an alternate embodiment, conjugate 5b in FIG. 2C was prepared by saponification and coupling of the peptide 4b (Boc-Leu-$^D$Phe-Pro-Val-Orn(Cbz)-OMe) with 4-AT. Similarly, conjugate 5c in FIG. 2C was prepared by coupling the (E)-alkene isostere as indicated as compound 3 in FIG. 2C with 4-AT. These peptide and peptide analogs are additional examples of suitable targeting sequences having an affinity to the mitochondria of a cell.

In another embodiment, peptide isosteres may be employed as the conjugate. Among the suitable peptide isosteres are trisubstituted (E)-alkene peptide isosteres and cyclopropane peptide isosteres, as well as all imine addition products of hydro- or carbometalated internal and terminal alkynes for the synthesis of di and trisubstituted (E)-alkene and cyclopropane peptide isosteres. See Wipf et al., 2005b. These peptide mimetics have been found to act as β-turn promoters. See Wipf et al., 2005b.

The linker, R2, may be any useful linker, chosen for its active groups, e.g., carboxyl, alkoxyl, amino, sulfhydryl, amide, etc. Typically, aside from the active groups, the remainder is non-reactive (such as saturated alkyl or phenyl), and does not interfere, sterically or by any other physical or chemical attribute, such as polarity or hydrophobicity/hydrophilicity, in a negative (loss of function) capacity with the activity of the overall compound. In one embodiment, aside from the active groups, the linker comprises a linear or branched saturated $C_4$-$C_{20}$ alkyl. In one embodiment, the linker, R2 has the structure

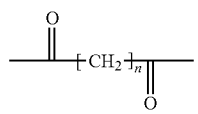

In which n is 4-18, including all integers therebetween, in one embodiment, 8-12, and in another embodiment, 10.

A person skilled in the organic synthesis arts can synthesize these compounds by crosslinking groups R1 and R3 by any of the many chemistries available. In one embodiment, R1 and R3 are to R2 by an amide linkage (peptide bond) formed by dehydration synthesis (condensation) of terminal carboxyl groups on the linker and an amine on R1 and R3 (or vice versa). In one embodiment, R1 and R3 are identical or different and are selected from the group consisting of: XJB-5-131, XJB-5-125, XJB-7-75, XJB-2-70, XJB-2-300, XJB-5-208, 197, XJB-5-194, JP4-039 and JP4-049, attached in the manner shown in FIGS. 2C and 2D.

Further examples of compounds which may be used according to this invention include, but are not limited to, compounds set forth in US 20070161544 and US20070161573 (incorporated by reference in their entireties herein), such as, for example, XJB-5-131.

5.2 Signs of Aging that May be Modulated

The present invention may be used to inhibit the occurrence, progression and/or severity of one or more signs of aging, including, but not limited to, epidermal atrophy, epidermal hyperpigmentation, rhytid (wrinkles), photoaging of the skin, alopecia, hearing loss, visual impairment, cerebral atrophy, cognitive deficits, trembling, ataxia, areflexia, cerebellar degeneration, hypertension, renal insufficiency, renal acidosis, incontinence, endocrinopathies, diabetes, decreased liver function, hypoalbuminemia, hepatic accumulation of glycogen and triglycerides, anemia, bone marrow degeneration, osteopenia, osteoporosis, kyphosis, degenerative joint disease, intervertebral disc degeneration, peripheral neuropathy, impaired wound healing increased cellular senescence, retinal degeneration, motor neuron degeneration, cerebral lacunae, white matter degeneration, sarcopenia, muscle weakness, dystonia, increased peroxisome biogenesis, increased apoptosis, decreased cellular proliferation, cachexia, and decreased lifespan. "Inhibiting the occurrence, progression and/or severity of a sign of aging" means reducing the risk of occurrence, delaying the onset, slowing the progression, and/or reducing the severity and/or manifestation, of a sign of aging, and includes, but is not limited to, preventing the occurrence, development or progression of a sign of aging.

The present invention may be used to improve age-related performance in a subject. "Improving performance" refers to any aspect of performance, including cognitive performance or physical performance, such as, but not limited to, the ability to be self-sufficient, to take care of (some but not necessarily all) personal needs, to be ambulatory or otherwise mobile, or interaction with others. In non-limiting embodiments, the present invention may be used to treat young individuals to prevent age-related disease, and/or to treat young patients who have early onset aging symptoms. A "young" individual, where the individual is a human, is less than about 60 years old, preferably between 10-59 years old, or between 20-50 years old. The present invention may also be used to treat patients with syndromes of accelerated aging, e.g., progeria.

The present invention may be used to prolong the lifespan or healthspan of a geriatric subject, for example, relative to an age-matched, clinically comparable control not treated according to the invention.

5.3 Methods of Treatment

Accordingly, in one set of embodiments, the present invention provides for a method of inhibiting one or more signs of aging in a subject in need of such treatment, comprising administering, to the subject, an effective amount of a compound as set forth above. "Inhibiting a sign of aging" means reducing the risk of occurrence, delaying the onset, slowing the progression, and/or reducing the severity and/or manifestation, of a sign of aging, and includes, but is not limited to, preventing the occurrence, development or progression of a sign of aging.

In a related set of non-limiting embodiments, the present invention provides for a method of improving age-related performance in a subject, comprising administering to the subject an effective amount of a compound as set forth above.

In one non-limiting embodiment, the present invention provides for a method of inhibiting a sign of aging in a young individual comprising administering to the subject an effective amount of a compound as set forth above.

In one non-limiting embodiment, the present invention provides for a method of treating an early onset aging symptom in a young patient comprising administering to the subject an effective amount of a compound as set forth above. In another non-limiting embodiment, the present invention provides for a method of treating an accelerated aging syndrome in a subject in need of such treatment comprising administering to the subject an effective amount of a compound as set forth above, wherein the accelerated aging syndromes include, but are not limited to, progerias. A "young" individual, where the individual is a human, is less than about 60 years old, preferably between 10-59 years old, or between 20-50 years old.

In another related set of embodiments, the present invention provides for a method of prolonging survival of a geriatric subject, comprising administering, to the subject, an effective amount of a compound as set forth above.

In yet another set of embodiments, the present invention provides for a method of inhibiting the occurrence, progression or severity of a degenerative disorder in a subject in need of such treatment, including but not limited to, a subject suffering from a neurodegenerative disorder such as Alzheimer's Disease, Parkinson's Disease, Amyotrophic Lateral Sclerosis, Huntington's Chorea, and Lewy Body Disease, osteoporosis, or a joint degenerative disorder, such as osteoarthritic or rheumatoid arthritis, or intervertebral disc degeneration comprising administering, to the subject, an effective amount of a compound as set forth above. The person skilled in the art would be aware of the appropriate indicia to measure to assess whether progression has been inhibited for each of said degenerative disorders. Non-limiting specific examples of indicia of neurodegeneration include impaired cognition, impaired short term memory, dystonia, trembling, choreoform movements, weakness, spasticity, decreased nerve conduction, ataxia, visual impairment, peripheral neuropathy and hearing loss. "Inhibiting the occurrence, progression or severity of a degenerative disorder" means reducing the risk of occurrence, delaying the onset, slowing the progression, and/or reducing the severity and/or manifestation, of a degenerative disorder, and includes, but is not limited to, preventing the occurrence, development or progression of a degenerative disorder.

The compound may be administered systemically to achieve distribution throughout the body or may be administered to achieve a local effect. The route of administration may be selected depending on the intended effect. As non-limiting examples, systemic administration, to achieve therapeutic levels throughout the body, may be achieved using an inhibitor suitable for distribution throughout the body, administered via any standard route, including but not limited to oral, intravenous, inhalation, intraperitoneal, subcutaneous, or intramuscular routes. Non-limiting examples of local administration include, but are not limited to, intrathecal administration to treat central nervous system manifestations of aging, ocular instillation to treat visual disturbances, intramuscular injection may be used to treat muscle wasting, topical administration to prevent or reverse skin aging etc.

In one embodiment, the present invention provides for a method of preventing, delaying or attenuating loss of vision due to cataracts, leucoma, glaucoma or retinal degeneration in a subject in need of such treatment comprising administering, to the subject, an effective amount of a compound as set forth above.

In one embodiment, the present invention provides for a method of treating accelerated aging syndromes in a subject in need of such treatment comprising administering, to the subject, an effective amount of a compound as set forth above, wherein the accelerated aging syndromes include, but are not limited to progerias. In another embodiment, the present invention provides for a method of treating genome instability disorder in a subject in need of such treatment comprising administering, to the subject, an effective amount of a compound as set forth above, wherein the genome instability disorder causes accelerated aging of one or more tissues.

In yet another embodiment, the present invention provides for a method of treating accelerated aging syndrome in a subject who has undergone cancer therapy comprising administering, to the subject, an effective amount of a compound as set forth above. In one embodiment, the accelerated aging syndrome suffered by the subject is due to excessive DNA damage caused by the cancer therapy undergone by the subject. Accelerated aging symptoms include but are not limited to, peripheral neuropathy, hair loss, greying, epidermal atrophy, poor wound healing, muscle wasting, loss of hearing, osteoporosis, trembling and cognitive deficits.

In yet another embodiment, the present invention provides for a method of preserving or improving quality and function of cell products which are intended for therapy in a subject, which method comprises administering an effective amount of a compound as set forth above to the cells prior to administering the cell products to the subject. The therapies include, but are not limited to, stem cell therapy, ips cell therapy, grafting, and autologous therapies.

Topical formulations may include administering the compound as set forth above, optionally comprised in microsphere, microcapsule, or liposome, in a cream, lotion, organic solvent, or aqueous solution.

Compounds as set forth herein may be administered in a suitable pharmaceutical carrier (e.g. sterile water, normal saline, phosphate buffered saline, etc.). Not by way of limitation, inhibitors may be administered as a solution, as a suspension, in solid form, in a sustained release formulation, in a topical cream formulation, etc. In particular non-limiting examples, an inhibitor may be incorporated into a microcapsule, nanoparticle or liposome. For certain compounds, including, but not limited to, XJB-5-131, which are sparingly soluble, it may be desirable to use, as a carrier, an agent that promotes penetration through a cell membrane, such as, but not limited to, dimethylsulfoxide.

An effective dose/amount may be calculated by determining the amount needed to be administered to produce a concentration sufficient to achieve the desired effect in the tissue to be treated, taking into account, for example, route of administration, bioavailability, half-life, and the concentration which achieves the desired effect in vitro or in an animal model system, using techniques known in the art.

Non-limiting examples of doses of compounds, as set forth herein, include between 0.1 and 50 mg/kg, or between 1 and 25 mg/kg, or between 2 and 20 mg/kg, or about 2 mg/kg, or about 10 mg/kg, which may be administered daily, at least 5 times a week, at least 3 times a week, at least twice a week, at least once a week, at least twice a month, at least once a month, at least once every three months, or at least once every six months.

In particular, non-limiting embodiments, a subject may be treated with a compound as set forth herein, using a regimen comprising a loading period followed by a maintenance period, wherein the loading period includes treatment, with 1-20 mg/kg or 2-10 mg/kg, daily or every other day for a period of 5-10 days, followed by a maintenance period which includes 1-10 mg/kg, or 10-50 mg/kg, given once a week, twice a week, three times a week, every other week, or once a month.

In other specific non-limiting embodiments where XJB-5-131 is the compound, the dose may be between about 0.1 and 20 mg/kg, or between about 0.3 and 10 mg/kg, or between about 2 and 8 mg/kg, or about 2 mg/kg;

where either JP4-039, JED-E71-37 or JED-E71-58 is the compound, the dose may be between about 0.01 and 50 mg/kg, or between about 0.1 and 20 mg/kg, or between about 0.3 and 10 mg/kg, or between about 2 and 8 mg/kg, or about 2 mg/kg;

a combination of any of the foregoing regimens may also be used; and in any of the foregoing, the dose may be administered daily, at least 5 times a week, at least 3 times a week, at least twice a week, at least once a week, at least twice a month, at least once a month, at least once every three months, or at least once every six months.

6. EXAMPLES

6.1. Example 1

A Murine Model of Aging

ERCC1-XPF is a DNA repair endonuclease that is essential for nucleotide excision repair of bulky DNA adducts and the repair of DNA interstrand crosslinks, and contributes to the repair of double-strand breaks (Sijbers et al., 1996; Niedernhofer et al., 2004; Ahmad et al., 2008). The two proteins are obligate binding partners required to stabilize one another in vivo (Niedernhofer et al., 2006) and are thought to function exclusively as a nuclease in DNA repair (Sgouros et al., 1999). Mutations in Xpf that severely affect expression of ERCC1-XPF cause dramatically accelerated aging in humans including the epidermal, hematopoietic, endocrine, hepatobiliary, nervous, musculoskeletal and cardiovascular systems (Niedernhofer et al., 2006). There are strong parallels between this progeroid syndrome and other diseases caused by inherited defects in genome maintenance mechanisms including Werner syndrome, Cockayne syndrome, trichothiodystrophy, xeroderma pigmentosum, Rothmund Thompson syndrome and ataxia telangiectasia, all of which include accelerated aging of one or more tissues (Hasty et al., 2003). This accelerated aging is generally accepted to be due to the accumulation of unrepaired DNA damage (Garinis et al., 2008; Garinis et al., 2009).

As in humans, genetic depletion of Ercc1 or Xpf in the mouse causes a severe phenotype (McWhir et al., 1993; Tian et al., 2004; Weeda et al., 1997). $Ercc1^{-/-}$ and $Xpf^{-/-}$ mice die in the fourth week of life with symptoms associated with advanced age, including ataxia, kyphosis, weight loss, epidermal atrophy, sarcopenia, bone marrow degeneration, liver and kidney dysfunction, and evidence of replicative senescence (Niedernhofer et al., 2006; Weeda et al., 1997; Prasher et al., 2005). The comparison of $Ercc1^{-/-}$ mice to naturally aged mice revealed a highly significant correlation between the two at the level of physiology, histopathology and genome-wide expression patterns (Niedernhofer et al., 2006), which established these DNA repair deficient mice as an accurate but accelerated model of natural aging, pertinent to humans because it mimics a human progeria. If the capacity to repair stochastic molecular damage is an important determinant of lifespan, then the prediction is that organisms with reduced capacity for repair would have proportionally reduced lifespan. However, the extremely short lifespan of these mice makes interventional studies to probe the mechanism of aging impractical. To test this, a series of mice were generated expressing various levels of ERCC1-XPF DNA repair endonuclease and therefore different capacities for DNA repair and lifespan. Hypomorphic and conditional ERCC1 mutants were cloned (FIG. 3). The hypomorphic allele (A) contains a deletion of the last 7 amino acids of ERCC1 to humanize the protein. Transcriptional interference from the neomycin cassette in the last intron of the gene reduces the stability of the Ercc1 mRNA by 6-fold (Weeda et al., 1997). In the second construct (cond), genomic sequence of Ercc1 exon 7 was fused to a cDNA encoding exons 8-10, and the fusion was floxed with loxP sites to allow tissues specific deletion of ERCC1 in the mouse.

$Ercc1^{-/\Delta}$ compound heterozygote mice were bred and tissues isolated for analysis. Direct detection of ERCC1 protein is not currently possible due to the lack of an antibody that recognizes the murine protein. As a surrogate, XPF, the obligate binding partner of ERCC1, was measured in mouse liver (FIG. 4). XPF levels in $Ercc1^{-/\Delta}$ mice were 10% that of wild type mice. In accordance, cells from the $Ercc1^{-/\Delta}$ had an intermediate sensitivity to DNA damage agents relative to congenic wild type and ERCC1-null cells (FIG. 5). Furthermore, $Ercc1^{-/\Delta}$ mice had an intermediate lifespan relative to wild type littermates and ERCC1 knock-out mice (FIG. 6A-D).

Figure 6B:
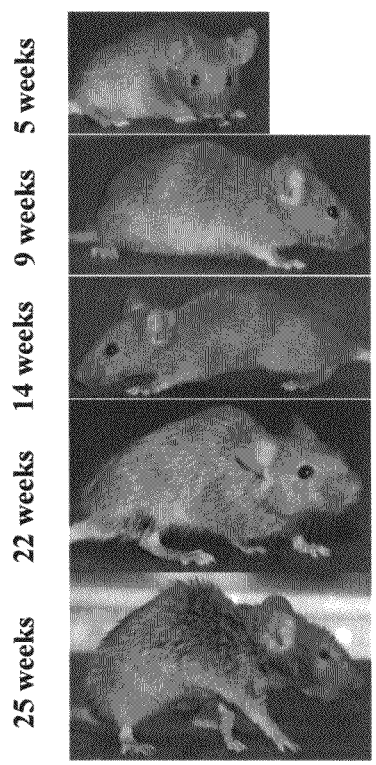

A cohort of $Ercc1^{-/\Delta}$ mice were allowed to live their full lifespan and monitored for symptoms associated with advanced age (FIG. 6B). $Ercc1^{-/\Delta}$ mice developed the same progeroid symptoms as $Ercc1^{-/-}$ mice (and patients expressing low levels of ERCC1-XPF; FIG. 6C). However, the age at onset of symptoms was delayed from perinatal in Ercc1–/– mice to 8 weeks of age in $Ercc1^{-/\Delta}$ mice (FIG. 6D). The $Ercc1^{-/\Delta}$ mice were healthy for the first 8-9 weeks of life, then began to show numerous spontaneous and progressive symptoms associated with aging including signs of neurodegeneration, muscle wasting, loss of vision and hearing, urinary incontinence, epidermal atrophy, bone marrow failure, decreased liver and kidney function, loss of β islet cells, osteoporosis and intervertebral disc degeneration. FIG. 6D illustrates their accelerated aging phenotype.

Genome-wide expression profiling in liver and pancreas of $Ercc1^{-/\Delta}$ mice established that the expression changes relative to wide type littermate controls were nearly identical to, yet less dramatic than those of $Ercc1^{-/-}$ mice (Schumacher et al., 2008, which in turn correlated significantly to genome-wide expression changes seen with natural aging (Niedernhofer et al., 2006). This emphasizes the relevance of these models to natural aging.

6.2. Example 2

Protective Effects of XJB-5-131

To assess the effectiveness of XJB-5-131 in inhibiting degeneration and/or signs of aging and age-related degenerative diseases, the compound was administered, over a 18-21 week period, to progeroid $Ercc1^{-/\Delta}$ mice, at a dose of 2 mg/kg in sunflower seed oil carrier (to promote solubility) administered intraperitoneally three times per week (FIG. 7). Sunflower seed oil was administered to twin $Ercc1^{-/\Delta}$ mice according to the same schedule as a control. The treated and control mice were monitored twice a week for weight and symptom/sign development.

FIG. 8 presents a summary table showing the age at onset of progeroid symptoms in $Ercc1^{-/\Delta}$ mice treated one example of the compounds as disclosed herein, XJB-5-131 or vehicle only (oil). The aging score reflected the relative age at onset of progeroid symptoms in one mouse treated with XJB-5-131 vs. its sibling treated with oil only and was thus a measure of healthspan. In addition to improvement in most signs measured, the overall aging score was significantly improved in the XJB-5-131-treated mice. Treating $Ercc1^{-/\Delta}$ mice with XJB-5-131 delayed the onset of progeroid symptoms and aging pathologies. Of note, all of the signs of neurodegeneration, including dystonia, trembling, ataxia, wasting and urinary incontinence, were delayed in the treated animals providing strong evidence that XJB-5-131 protects neurons against degenerative changes caused by oxidative stress.

Figure 9A:
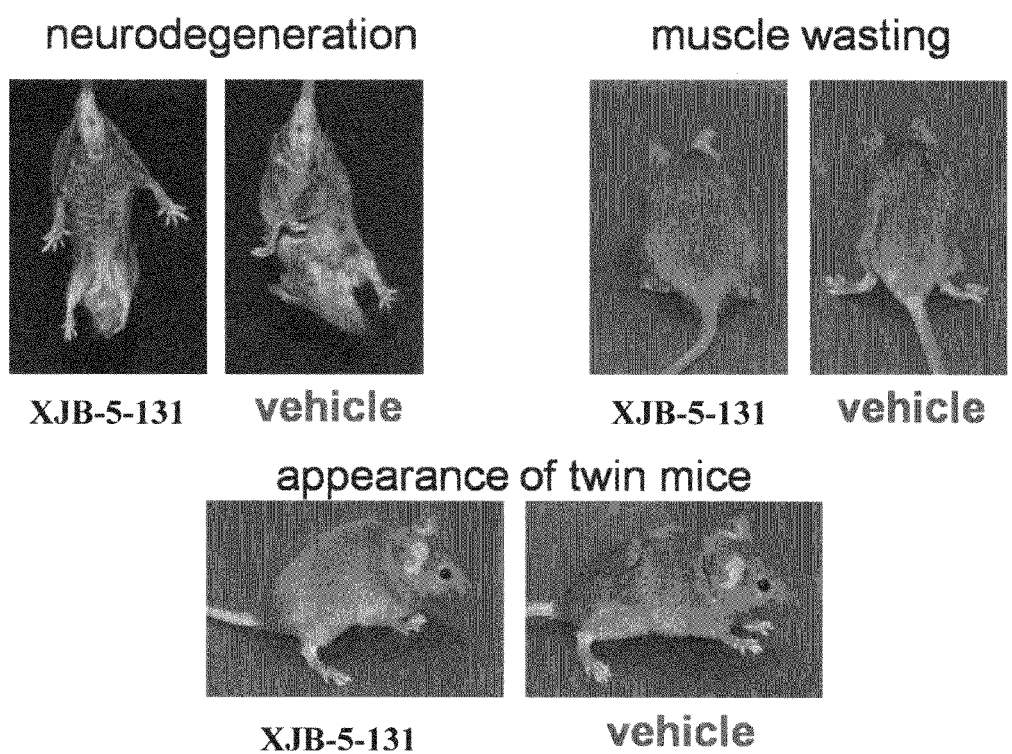

FIG. 9A shows examples of twin ERCC1-deficient mice where one mouse was treated with XJB-5-131 and its sibling received vehicle only. The mouse treated with XJB-5-131 showed reduced neurodegeneration and muscle wasting as well as improved appearance.

Figure 9B:
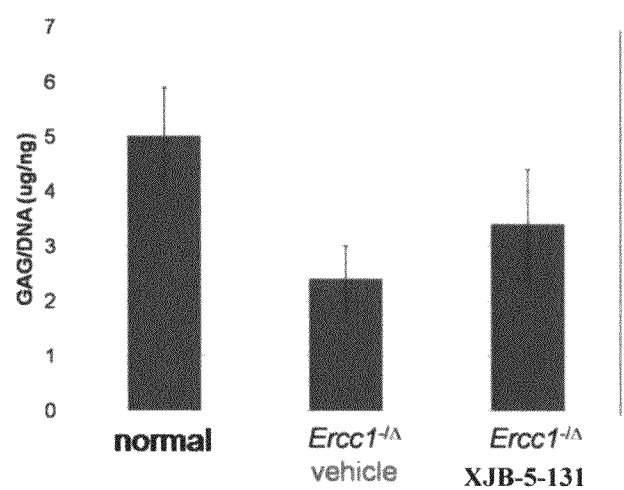
Figure 9C:
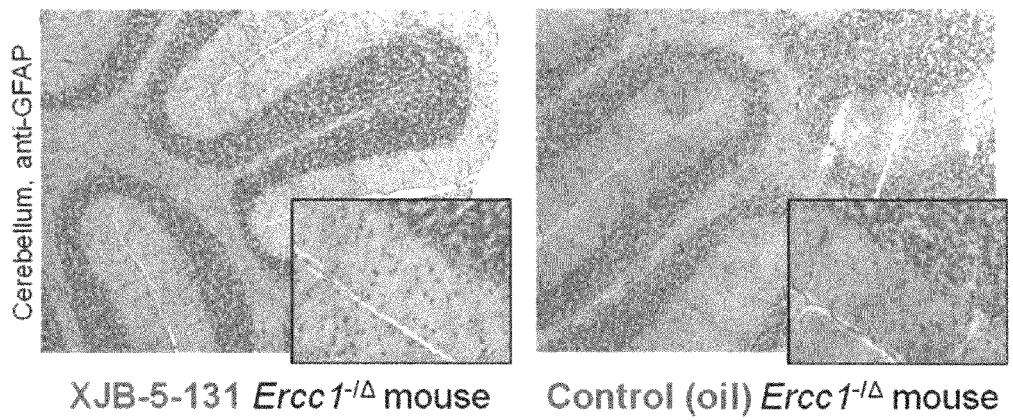
Figure 9D:
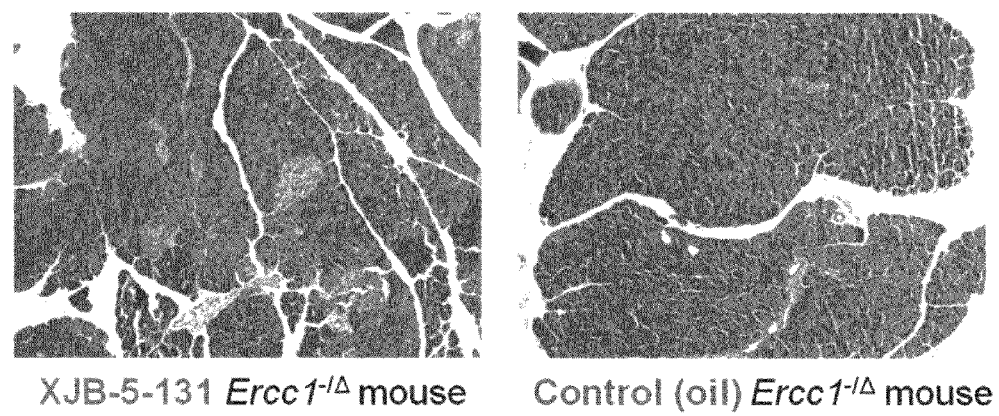

To assess the ability of XJB-5-131 to inhibit deterioration of intervertebral discs (an index of degenerative disease of the vertebrae), the level of glycosaminoglycan, an extra-cellular matrix protein that is essential for disc maintenance and flexibility, in the discs in treated and control mice were measured, and the results are shown in FIG. 9B. The intervertebral discs of treated mice contained approximately 30 percent more glycosaminoglycan relative to control mice, indicating delay of disc degeneration. In addition, immunohistochemical analysis of brains from mice demonstrated significantly reduced neurodegeneration in animals treated with XJB-5-131, compared to siblings treated with vehicle only (FIG. 9C). Also, XJB-5-131 treatment preserved insulin-producing B-islet cells in mice (FIG. 9D), cells necessary to prevent diabetes.

Figure 10A:
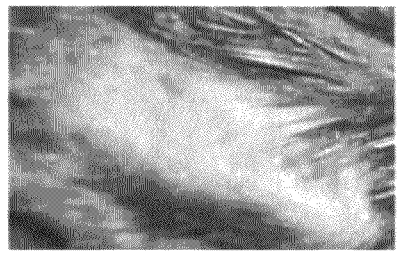
Figure 10A:
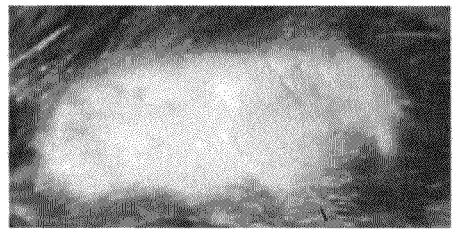
Figure 10B:
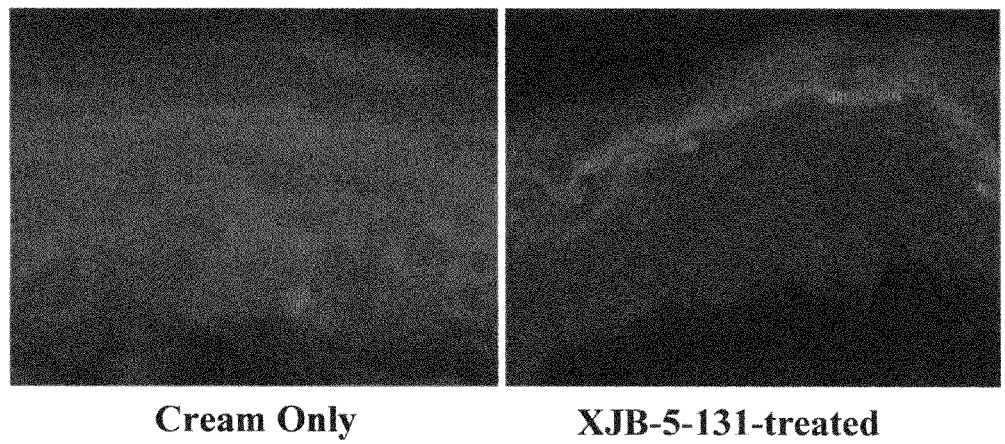
Figure 10C:
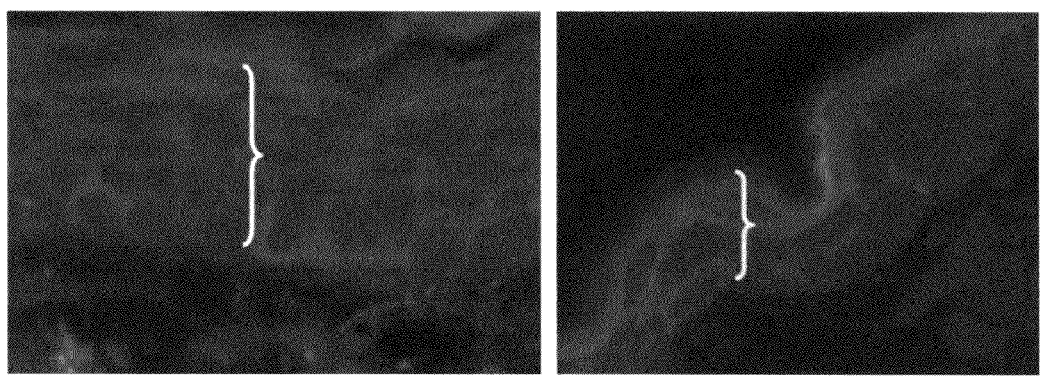

As a measure of the effect of XJB-5-131 on photoaging or sun-induced skin changes, treated and control $Ercc1^{-/cond}$. K 14-Cre mice, which are missing ERCC1 only in the skin, were shaved, treated with a depilatory, then irradiated with UV-B light to induce sunburn (500 J/m2, the median erythemal dose). Subsequently, the mice were treated with XJB-5-131 (80 μg) emulsified in a cream daily for five days. The results, shown in FIG. 10A, indicated that the skin of XJB-5-131-treated mice appeared much more smooth and healthy relative to cream-only treated control. In addition, immunofluorescence analysis of skin sections from these mice demonstrated that XJB-5-131 improved keratin and reduced inflammation of skin after acute or chronic photoaging (FIGS. 10B and C). In total, these data demonstrated the ability of a compound as disclosed herein to delay and ameliorate age-related degenerative changes of multiple organ systems.

At a macroscopic level, administration of XJB-5-131 appeared to have been well-tolerated by the animals, as indicated by the fact that they did not lose weight as a result of treatment. Graphs showing weight versus time of treated, untreated and control animals are shown in FIG. 11A-B. XJB-5-131 did not cause weight loss, as does the parental control TEMPO. To assess the impact of XJB-5-131 at a cellular level, a number of experiments were carried out using mouse embryonic fibroblasts ("MEF") cells harvested from $Ercc1^{-/-}$ mouse embryos. As shown in FIG. 12, such MEF cultures were prepared and grown under ambient oxygen (oxidative stress) conditions, and then either untreated (media only) or treated with a concentration of 500 nM (in media) XJB-5-131, and then tested for SA-β galactosidase staining (a marker of cellular senescence). The amount of staining was notably less in the treated cells. In addition, XJB-5-131 treatment was found to reduce the number of γH2AX foci in DNA (a marker of double-stranded breaks; FIG. 13A), although it did not reduce the amount of apoptosis (FIG. 14).

6.3. Example 3

Protective Effects of JP4-039

To assess the therapeutic potential of one example of the compounds as disclosed herein, JP4-039, tests for safety and protective activity were performed. FIGS. 15 and 16 show the results of tests to evaluate whether varying concentrations of JP4-039 produce toxic effects after 48 hours in cultures of MEF cells prepared from $Ercc1^{-/-}$ or wild-type mouse embryos, respectively. Even under the highest concentrations tested (10 μM), no signs of toxicity were observed in either culture system and cellular proliferation was enhanced relative to untreated control cells (media only).

Figure 10D:
Figure 10D:

To test the protective activity of JP4-039, cultures of primary MEF were prepared from $Ercc1^{-/-}$ mouse embryos and grown under 20% oxygen (ambient air), which creates oxidative stress in these cells that are hypersensitive to the reactive oxygen species. The cells were then either treated with a concentration of 1 μM of XJB-5-131, JP4-039, JED-E71-37 or JED-E71-58, or left untreated, and then after 48 hours the level of p16, a marker of irreversible cellular senescence, was measured by immunofluorescence staining. As seen in FIG. 17, the level of p16 was much lower in MEF cells treated with JP4-039 relative to its level in untreated cells, whereas XJB-5-131, JED-E71-37 and JED-E71-58 were observed to be less effective at this concentration. Furthermore, in vivo, JP4-039 reversed epidermal atrophy, by increasing proliferation of keratinocytes (FIG. 10D). Thus JP4-039 was efficacious in vitro and in vivo for reducing/reversing age-related degenerative changes.

6.4. Example 4

Protective Effects of the Compounds as Disclosed Herein in Cell Culture

To evaluate the protective activities of two examples of the compounds as disclosed herein, JED-E71-37 and JED-E71-58, primary MEF cells were prepared from $Ercc1^{-/-}$ mice and grown under conditions of oxidative stress (ambient air, 20% oxygen). The cells were then either untreated or treated with 1 μM JED-E71-37 or JED-E71-58 for a period of 48 hours. As can be seen in FIG. 18, both compounds improved cell proliferation despite the oxidative stress.

Next, the abilities of these two compounds, as well as XJB-5-131 and JP4-039, each at a concentration of 1 μM, were tested for their ability to prevent cellular senescence in cell cultures prepared, and oxidatively stressed, as in the preceding paragraph. Treated as well as untreated cells were, after 48 hours, immunostained for γ-H2AX, a marker of DNA double-strand breaks as well as cellular senescence. Results for JED-E71-58 are shown in FIG. 13, showing a distinct decrease in γ-H2AX. JP4-039 was also similarly effective, but XJB-5-131 and JED-E71-37 were observed to be less effective at this concentration. These data demonstrated the ability of these compounds as disclosed herein to attenuate two signs associated with aging (decreased cellular proliferation and increased cellular senescence).

6.5. Example 5

Protective Effects of XJB-5-131 in an Animal Model of Huntington's Disease

To further assess whether XJB-5-131 has a protective effect against neurodegeneration, the compound was tested in a second animal model. R6/2 mice model the neurodegenerative disease Huntington's disease.

Huntington's disease is a fatal autosomal dominant neurodegenerative disease. The prevalence of Huntington's disease is four to seven in 100 000 and it typically develops in mid-life. The symptoms involve psychiatric, motor and cognitive disturbances, and weight loss. Huntington's disease is caused by an expansion of a CAG repeat in exon 1 of the huntingtin gene, which encodes a protein suggested to be associated with synaptic vesicles and microtubules in neurons. Mutant huntingtin forms insoluble aggregates that accumulate in the cytoplasm and nucleus of cells, disrupting neuron function. R6/2 mice express exon 1 of the human huntingtin gene, containing 150 CAG repeats. Consequently, the mice develop neurological symptoms that resemble many of those seen in Huntington's disease, including deficits of motor co-ordination, altered locomotor activity, impaired cognitive performance and seizures. Symptoms begin by week 3-4 and are progressive. A small cohort (n=5) of R6/2 mice were treated with XJB-5-131 according to the scheme in FIG. 7 (2 mg/kg, intraperitoneally, three times per week beginning at 5 weeks of age). Motor co-ordination was measured using a rotarod, after the mice were conditioned to the apparatus. R6/2 mice treated with XJB-5-131 had significantly better motor coordination at 6 and 7 weeks of age than untreated mutant animals (FIG. 19). These data demonstrated that in a second animal model of neurodegeneration, XJB-5-131 was efficacious in delaying the progression of disease symptoms. Furthermore, the data indicated that the compounds as disclosed herein can specifically be used to treat Huntington's disease.

7. REFERENCES

Ahmad, A. et al., (2008) ERCC1-XPF endonuclease facilitates DNA double-strand break repair, Mol Cell Biol. 28, 5082-92.

Bao, J. J., et al., (2000) Elevated expression of hepatic proliferative markers during early hepatocarcinogenesis in hepatitis-B virus transgenic mice lacking mdr1a-encoded P-glycoprotein. Mol Carcinog, 29, 103-111.

Bartke, A. (2005) Minireview: role of the growth hormone/insulin-like growth factor system in mammalian aging. Endocrinology, 146, 3718-3723.

Bregegere, F., et al., (2006) The ubiquitin-proteasome system at the crossroads of stress-response and ageing pathways: a handle for skin care? Ageing Res Rev, 5, 60-90.

Brooks, P. J. (2002) DNA repair in neural cells: basic science and clinical implications. Mutat Res, 509, 93-108.

Browne, S. E., et al., (2004) Treatment with a catalytic antioxidant corrects the neurobehavioral defect in ataxia-telangiectasia mice. Free Radic Biol Med, 36, 938-942.

Chipchase, M. D., et al., (2003) Characterization of premature liver polyploidy in DNA repair (Ercc1)-deficient mice. Hepatology, 38, 958-966.

Crawley, J. N. (2000) What's wrong with my mouse? Wiley-Liss, New York.

Crippen, D. L. (2000) Preparing for an Aging Population. Committee on the Budget, U.S. House of Representatives, Washington, D.C.

Davé, S. H., et al., (2007) Amelioration of chronic murine colitis by peptide mediated transduction of the IkB kinase (IKK) inhibitor NEMO binding domain (NBD) peptide. Journal of Immunology, 179, 7852-7859.

De Bosscher et al. (2005) Proc. Natl. Acad. Sci. U.S.A., 102, 15827-15832.

de Boer, J., et al., (2002) Premature aging in mice deficient in DNA repair and transcription. Science, 296, 1276-1279.

Dolder, M. et al., (2001) Mitochondria creatine kinase in contact sites: Interaction with porin and adenine nucleotide translocase, role in permeability transition and sensitivity to oxidative damage, Biol. Signals Recept., 10, 93-111.

Dolle, M. E., et al., (2002) Mutational fingerprints of aging. Nucleic Acids Res, 30, 545-549.

Ferguson, V. L., et al., (2003) Bone development and age-related bone loss in male C57BL/6J mice. Bone, 33, 387-398.

Finkel, T. and Holbrook, N. (2000) Oxidants, oxidative stress and the biology of aging. Nature 408, 239-247.

Garinis, G. A., et al., (2008) DNA damage and ageing: new-age ideas for an age-old problem, Nat Cell Biol. 10, 1241-7.

Garinis, G. A., et al., (2009) Persistent transcription-blocking DNA lesions trigger somatic growth attenuation associated with longevity, Nat Cell Biol. 11, 604-15.

Gupta, S. (2000) Hepatic polyploidy and liver growth control. Semin Cancer Biol, 10, 161-171.

Hamilton, M. L., et al., (2001) Does oxidative damage to DNA increase with age? Proc Natl Acad Sci USA, 98, 10469-10474.

Hasty, P., et al., (2003) Aging and genome maintenance: lessons from the mouse? Science, 299, 1355-1359.

Heilbronn, L. K. and Ravussin, E. (2003) Calorie restriction and aging; review of the literature and implications for studies in humans, Am. J. Clin. Nutr. 78, 361-369.

Hekimi, S. and Guarente, L. (2003) Genetics and the specificity of the aging process. Science, 299, 1351-1354.

Hoye, A T et al., Targeting Mitochondria, *Accounts of Chemical Research* (2008) 41(1):87-97

Imai, H. et al., (2003) Protection from inactivation of the adenine nucleotide translocator during hypoglycaemia-induced apoptosis by mitochondria/phospholipid hydroperoxide glutathione peroxidase, Biochem. J., 371, 799-809.

Iverson et al., (2003) The cardiolipin-cytochrome c interaction and the mitochondria regulation of apoptosis, Arch. Biochem. Biophys. 423, 37-46.

Iverson, S. L. and S. Orrenius (2003) The cardiolipincytochrome c interaction and the mitochondria) regulation of apoptosis, Arch. Biochem. 423, 37-46.

Jiang, J, et al., "Structural Requirements for Optimized Delivery, Inhibition of Oxidative Stress, and Antiapoptotic Activity of Targeted Nitroxides," *The Journal of Pharmacology and Experimental Therapeutics* (2007) 320(3):1050-60 Kagan, V. E. et al., (2005a) Cytochrome C acts as a cardiolipin oxygenase required, for release of proapoptotic, factors, Nature Chem. Biol. 1, 23-232.

Kagan, V. E. et al., (2005b) Oxidative lipidomics of apoptosis: redox catalytic interactions of cytochrome c with cardiolipin and phosphatidylserine, Free Rad. Biol. Med. 37, 1963-1985.

Keller, H. L., et al., (1999) Association of IGF-I and IGF-II with myofiber regeneration in vivo. Muscle Nerve, 22, 347-354.

Kelso et al. (2001) Selective Targeting of a Redox-active Ubiquinone to Mitochondria within Cells: Antioxidant and Antiapoptotic Properties, J. Biol. Chem. 276,4588.

Kentner et al., (2002) Early Antioxidant Therapy with TEMPOL during Hemorrhagic Shock Increases Survival in Rats, J. of Trauma Injury, Infection, and Critical Care, 968.

Kenyon, C. (2005) The plasticity of aging: insights from long-lived mutants. Cell, 120, 449-460.

Kirkwood, T. B. (2005a) Time of our lives. What controls the length of life? EMBO Rep, 6 Spec No, S4-8.

Kirkwood, T. B. (2005b) Understanding the odd science of aging. Cell, 120, 437-447.

Kovalovich, K., et al., (2000) Increased toxin-induced liver injury and fibrosis in interleukin-6-deficient mice. Hepatology, 31, 149-159.

Kurosu, H., et al., (2005) Suppression of aging in mice by the hormone Klotho. Science, 309, 1829-1833.

Lantinga-van Leeuwen, I. S., et al., (2004) Lowering of Pkd1 expression is sufficient to cause polycystic kidney disease. Hum Mol Genet, 13, 3069-3077.

Liou, Y. C., et al., (2003) Role of the prolyl isomerase Pin1 in protecting against age-dependent neurodegeneration. Nature, 424, 556-561.

Louw et al., (1997) Biochem. Pharmacol., 53, 189-197.
Louw et al., (1999) Endocrinol., 140, 2044-2053.
Maier, B., et al., (2004) Modulation of mammalian life span by the short isoform of p53. Genes Dev, 18, 306-319.
McWhir, J. et al., (1993) Mice with DNA repair gene (ERCC-1) deficiency have elevated levels of p53, liver nuclear abnormalities and die before weaning. Nat Genet, 5, 217-224.
Mi, Z. et al., (2000) Characterization of a class of cationic peptides able to facilitate efficient protein transduction in vitro and in vivo. Mol Ther, 2, 339-347.
Michalopoulos, G. K. and DeFrances, M. (2005) Liver regeneration. Adv Biochem Eng Biotechnol, 93, 101-134.
Migliaccio, E. et al., (1999) The p66shc adaptor protein controls oxidative stress response and life span in mammals. Nature, 402, 309-313.
Mustafa, I. and Leverve, X. (2001) Metabolic and nutritional disorders in cardiac cachexia. Nutrition, 17, 756-760.
Niedernhofer, L. J. et al., (2006) A new progeroid syndrome reveals that genotoxic stress suppresses the somatotroph axis. Nature, 444, 1038-1043.
Niedernhofer, L. J. et al., (2004) The structure-specific endonuclease Ercc1-Xpf is required to resolve DNA interstrand cross-link-induced double-strand breaks. Mol Cell Biol, 24, 5776-5787.
Park, K. C. et al., (2005) Therapeutic effects of PG201, an ethanol extract from herbs, through cartilage protection on collagenase-induced arthritis in rabbits. Biochem Biophys Res Commun 331(4) 1469-77.
Parrinello, S. et al., (2003) Oxygen sensitivity severely limits the replicative lifespan of murine fibroblasts. Nat Cell Biol, 5, 741-747.
Pikarsky, E. et al., (2004) NF-kappaB functions as a tumour promoter in inflammation-associated cancer. Nature, 431, 461-466.
Prasher, J. M. et al., (2005) Reduced hematopoietic reserves in DNA interstrand crosslink repair-deficient Ercc1-/- mice. Embo J, 24, 861-871.
Resnick, N. M. and Dosa, D. (2004) Geriatric Medicine. In Kasper, D. L., Braunwald, E., Fauci, A. S., Hauser, S. L., Longo, D. L. and Jameson, J. L. (eds.), Harrison's Principles of Internal Medicine. McGraw-Hill, Montreal, pp. 249-259.
Rolig, R. L. and McKinnon, P. J. (2000) Linking DNA damage and neurodegeneration. Trends Neurosci, 23, 417-424.
Roubenoff, R. (1999) The pathophysiology of wasting in the elderly. J Nutr, 129, 256S-259S.
Rowlatt, C. et al., (1976) Lifespan, age changes and tumour incidence in an ageing C57BL mouse colony. Lab Anim, 10, 419-442.
Schumacher, B. et al., (2008) Delayed and accelerated aging share common longevity assurance mechanisms, PLoS Genet. 4, e1000161.
Selfridge, J. et al., (2001) Correction of liver dysfunction in DNA repair-deficient mice with an RCC1 transgene. Nucleic Acids Res, 29, 4541-4550.
Sgouros, J. et al., (1999) A relationship between a DNA-repair/recombination nuclease family and archaeal helicases, Trends Biochem Sci. 24, 95-7.
Sijbers, A. M. et al., (1996) Xeroderma pigmentosum group F caused by a defect in a structure-specific DNA repair endonuclease. Cell, 86, 811-822.
Shidoji, Y. et al., (1999) Loss of molecular interaction between cytochrome C and cardiolipin due to lipid peroxidation, Biochem. Biophys. Res. Comm. 264, 343-347.
te Poele, R. H. et al., (2002) DNA damage is able to induce senescence in tumor cells in vitro and in vivo. Cancer Res, 62, 1876-1883.
Tian, M et al., (2004) Growth retardation, early death, and DNA repair defects in mice deficient for the nucleotide excision repair enzyme XPF. Mol Cell Biol, 24, 1200-1205.
Tuominen, E. K. J., et al., (2002) Phospholipid cytochrome c interaction: evidence for the extended lipid anchorage, J. Biol. Chem. 277, 8822-8826.
U.S. Department of Health and Human Services, A.o.A. (2003) A profile of older Americans: 2003.
van der Pluijm, I. et al., (2007) Impaired genome maintenance suppresses the growth hormone—insulin-like growth factor 1 axis in mice with Cockayne syndrome. PLoS Biol, 5, e2.
Wadia, J. S. and Dowdy, S. F. (2002) Protein transduction technology. Curr Opin Biotechnol, 13, 52-56.
Weeda, G. et al., (1997) Disruption of mouse ERCC1 results in a novel repair syndrome with growth failure, nuclear abnormalities and senescence. Curr Biol, 7, 427-439.
Wipf, P. et al., (2005a) Mitochondria targeting of selective electron scavengers: synthesis and biological analysis of hemigramicidin-TEMPO conjugates, J. Am. Chem. Soc. 127:12460-12461.
Wipf et al., (2005b) Imine additions of internal alkynes for the synthesis of trisubstituted (E)-alkene and cyclopropane isosteres, ADV. SYNTH. CATAL. 347, 1605-1613

Various publications are cited herein, the contents of which are hereby incorporated by reference in their entireties.

What is claimed is:

1. A method of inhibiting free radical damage in a subject with Huntington's Disease or progeria, comprising administering to the subject an effective amount of a compound that reduces free radical damage in the mitochondria of the subject, wherein the compound is selected from

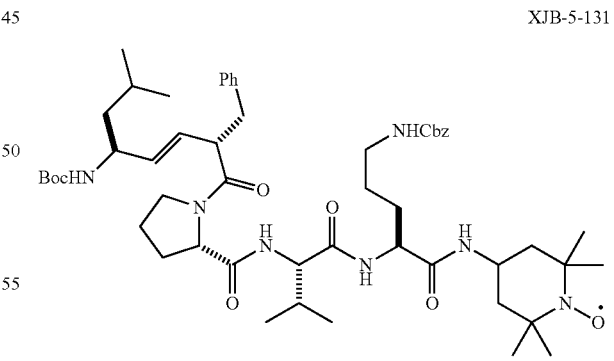

XJB-5-131

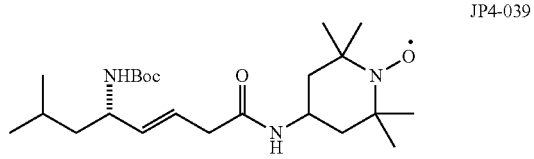

JP4-039

-continued
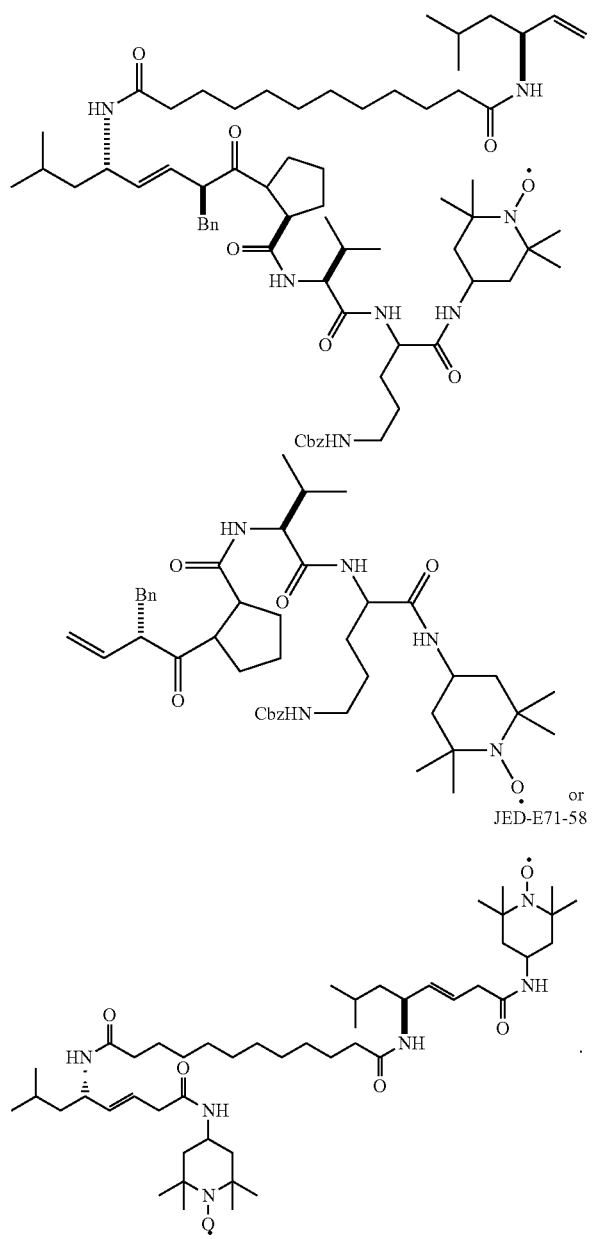
JED-E71-37
or
JED-E71-58
2. The method of claim 1, wherein the subject has Huntington's Disease.
3. The method of claim 2, and the compound that is administered to the subject is
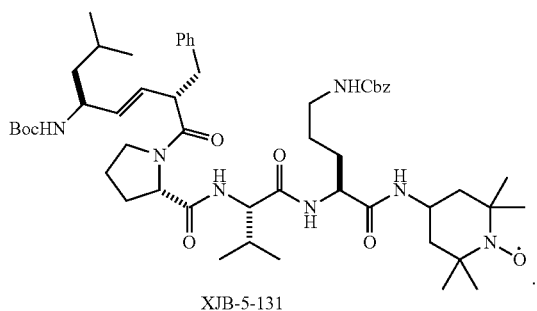
XJB-5-131
4. The method of claim 1, wherein the subject has progeria.
5. The method of claim 4, wherein the compound that is administered to the subject is
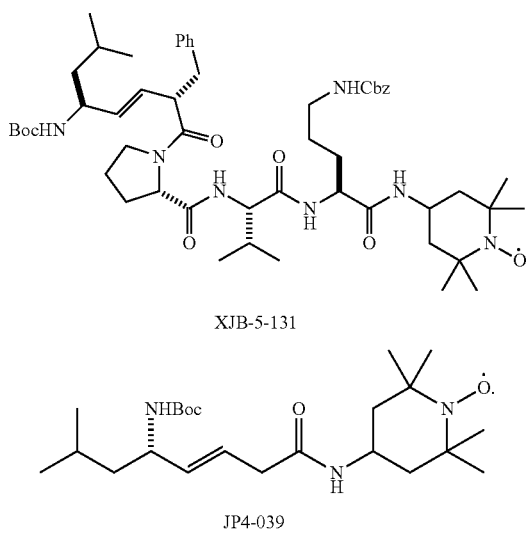
XJB-5-131
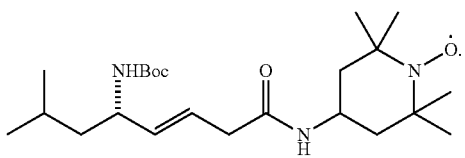
JP4-039
* * * * *